(12) United States Patent
Soreq et al.

(10) Patent No.: US 6,258,780 B1
(45) Date of Patent: Jul. 10, 2001

(54) METHOD AND COMPOSITION FOR ENABLING PASSAGE THROUGH THE BLOOD-BRAIN-BARRIER

(75) Inventors: Hermona Soreq, Jerusalem; Alon Friedman, M. Post HaNeguev; Shlomo Siedman, Neve Daniel; Daniela Kaufer, Mevasseret Zion, all of (IL)

(73) Assignee: Yissum Research Development Company, Jerusalem (IL)

( * ) Notice: Subject to any disclaimer, the term of this patent is extended or adjusted under 35 U.S.C. 154(b) by 0 days.

(21) Appl. No.: 08/975,084

(22) Filed: Nov. 20, 1997

Related U.S. Application Data

(60) Provisional application No. 60/053,200, filed on Jul. 21, 1997, provisional application No. 60/035,266, filed on Dec. 12, 1996, and provisional application No. 60/031,194, filed on Nov. 20, 1996.

(51) Int. Cl.[7] ........................ A61K 38/16; A61K 31/135; A61K 31/46; C12P 19/34
(52) U.S. Cl. ........................ 514/12; 530/224; 435/91.2
(58) Field of Search ................ 514/12; 530/324

(56) References Cited

U.S. PATENT DOCUMENTS 5,268,164 * 12/1993 Kozarich et al. .................. 424/9
5,434,137 * 7/1995 Black ................................ 514/15
5,686,416 * 11/1997 Kozarich et al. ................ 514/15

* cited by examiner

Primary Examiner—Michael Borin
(74) Attorney, Agent, or Firm—Kohn & Associates

(57) ABSTRACT

A pharmaceutical composition for facilitating passage of compounds through the blood-brain barrier comprising the agent ACHE-I4 readthrough (SEQ ID No:1) splice variant or the I4 peptide (SEQ ID No:2) and analogues of each thereof and a pharmaceutically acceptable carrier is disclosed. Alternatively, the pharmaceutical composition for facilitating passage of compounds through the blood-brain barrier can comprise the agents adrenaline, atropine, dopamine and/or an adrenergic combination and a pharmaceutically acceptable carrier. The composition can comprise at least two of the agents. The composition of the present invention can optionally include the compound to be transported across the blood-brain barrier. Alternatively, the compound can be co-administered (simultaneously) with the composition or can be administered at some point during the biologically effective period of the action of the composition. The present invention provides a method for administering a compound to the CNS of an animal by subjecting the animal to a stress-mimicking agent or treatment. This agent or treatment facilitates disruption of the blood-brain barrier. During the period that the BBB is opened or disrupted a compound can be administer such that the compound is enabled to passage through the disrupted BBB into the CNS.

10 Claims, 14 Drawing Sheets

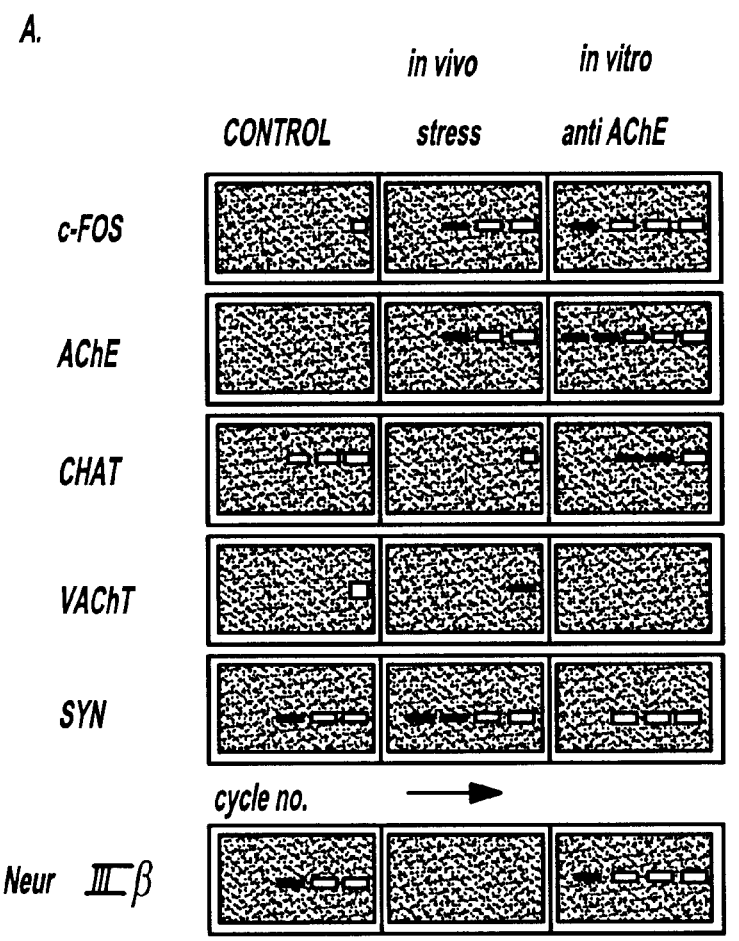
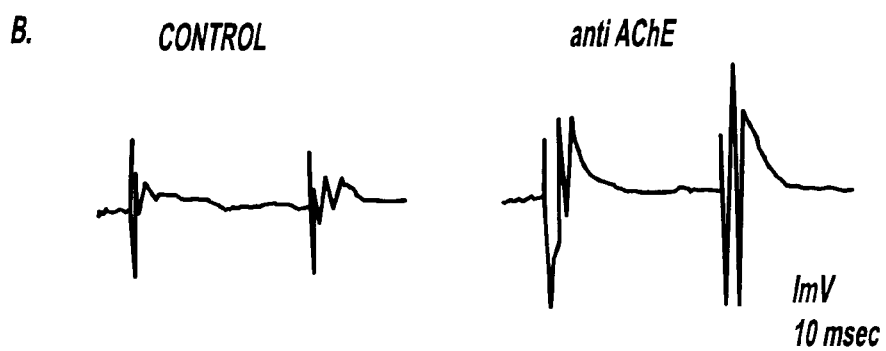
*Figure-3*

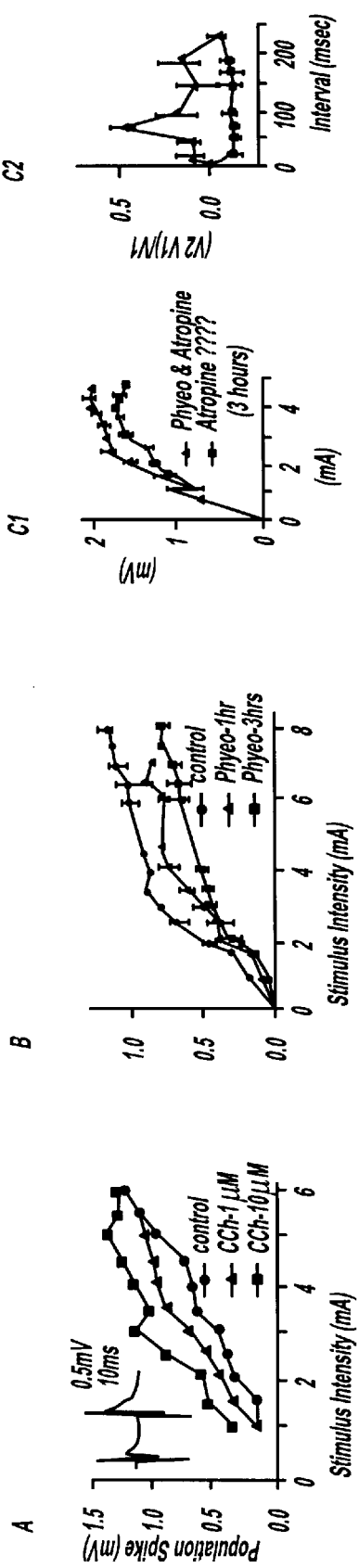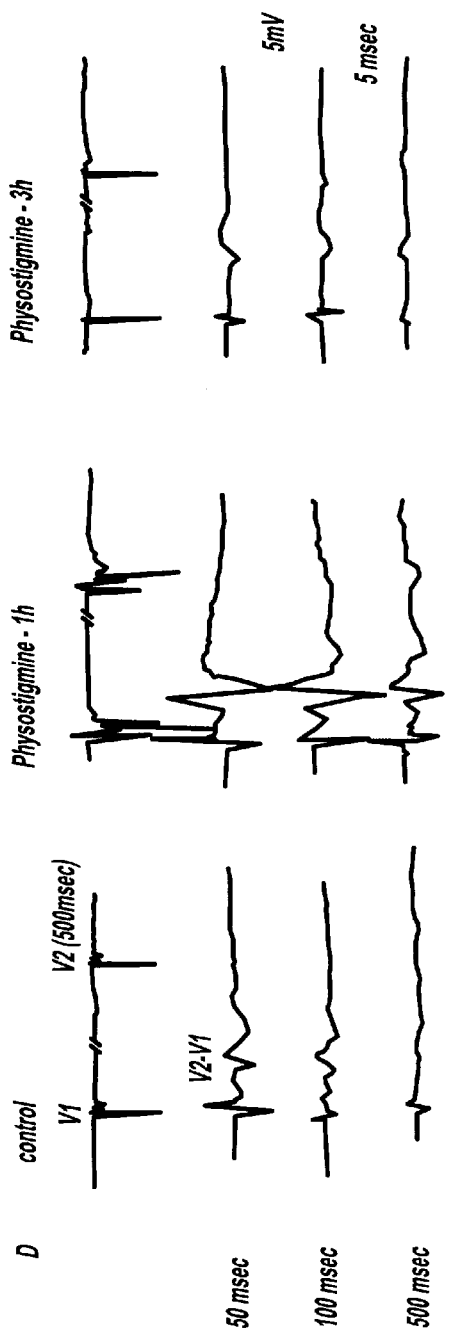
Figure-4

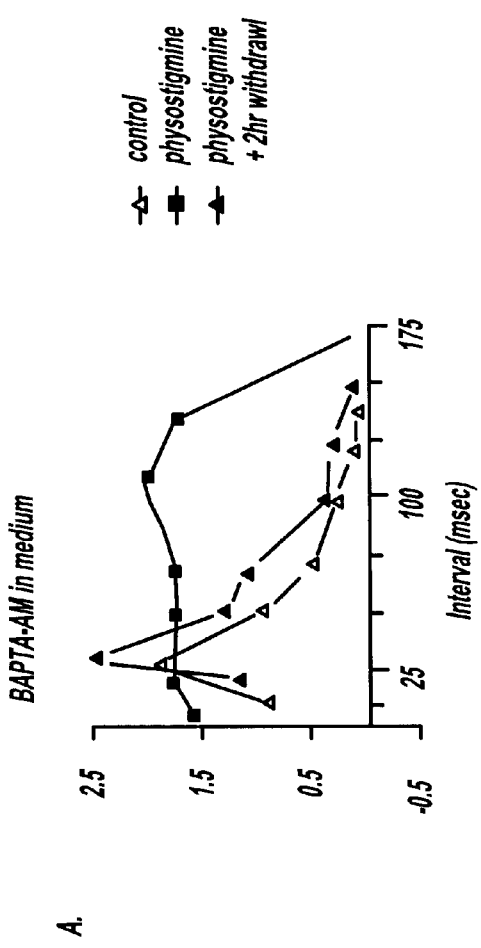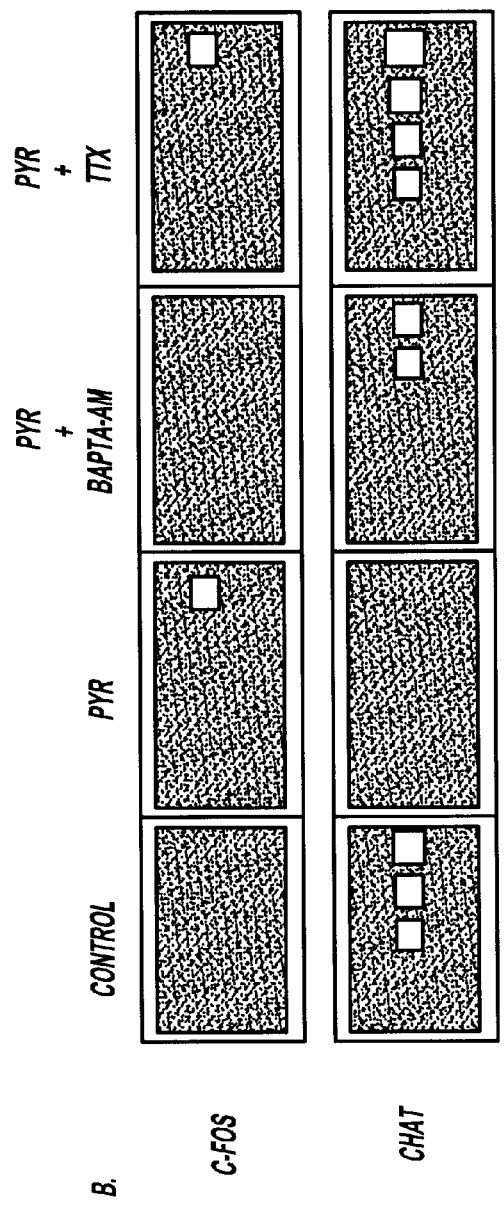
Figure-5

A. AChEmRNA variants
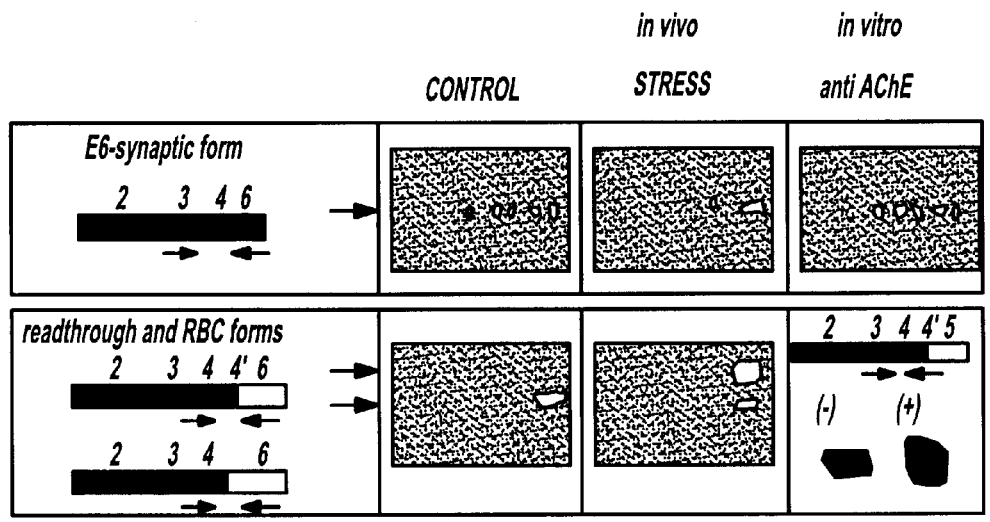
B. AChEmRNA in situ
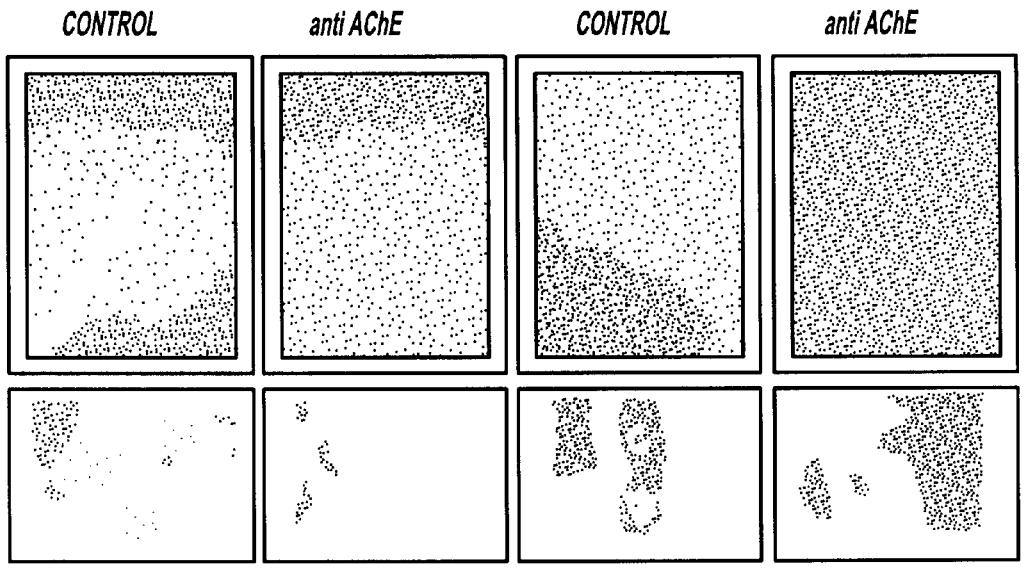
*Figure-7*

A. mRNA, IN VIVO
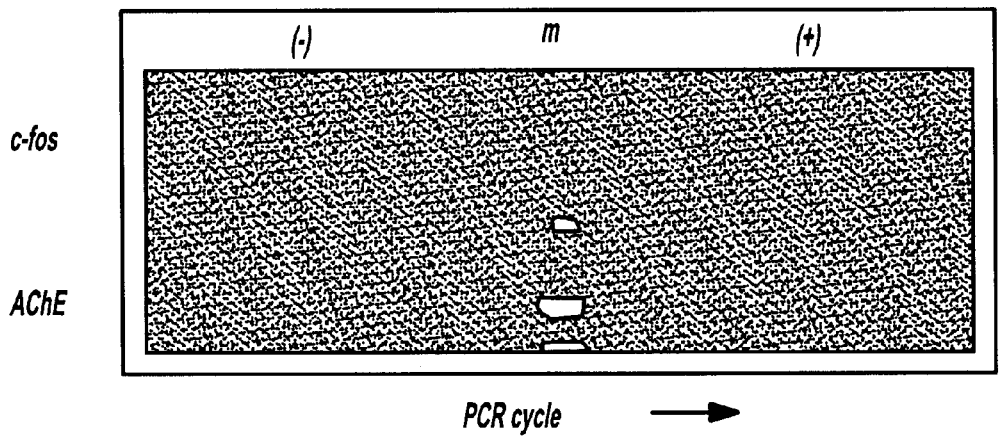
B. FIELD POTENTIALS, EX VITO
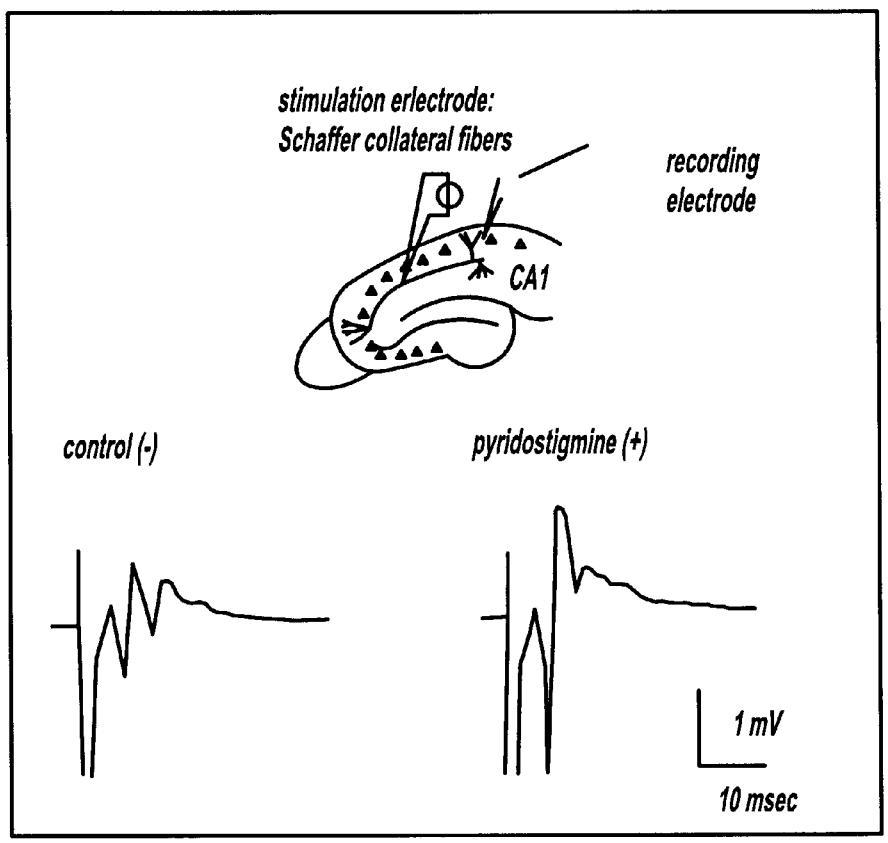
*Figure-10*

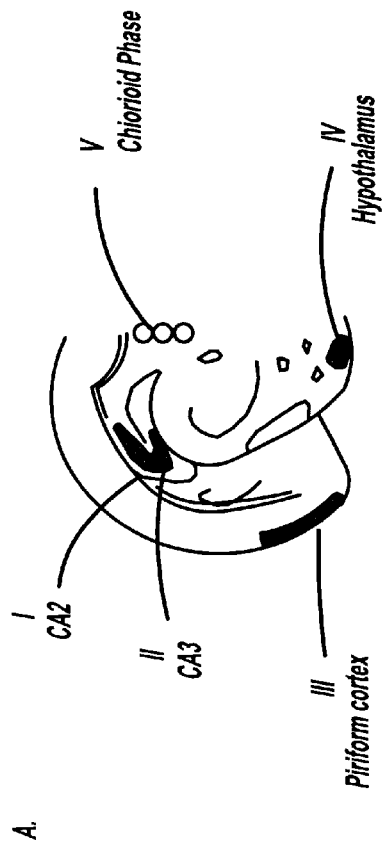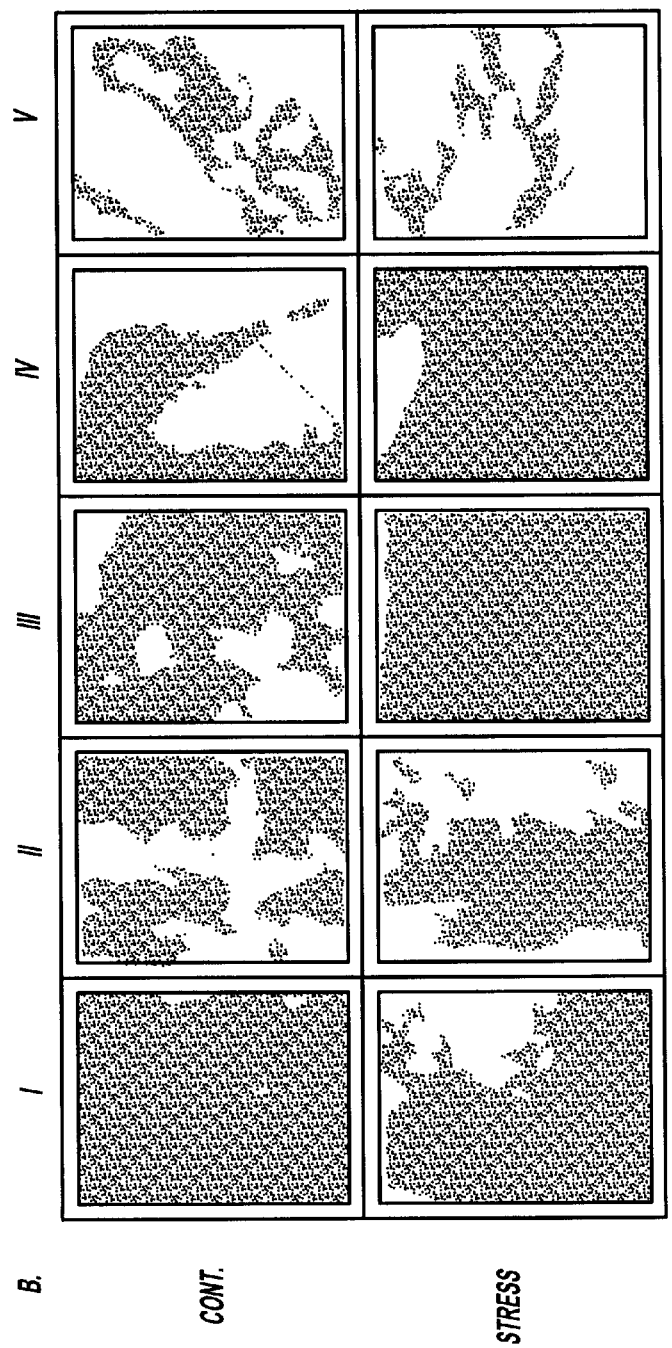
Figure 14

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 600 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

```
Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
            85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
            165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240
```

```
Gly Met His Leu Leu Ser Pro Pro Ser Arg Gly Leu Phe His Arg Ala
            245                 250                 255
Val Leu Gln Ser Gly Ala Pro Asn Gly Pro Trp Ala Thr Val Gly Met
        260                 265                 270
Gly Glu Ala Arg Arg Arg Ala Thr Gln Leu Ala His Leu Val Gly Cys
    275                 280                 285
Pro Pro Gly Gly Thr Gly Gly Asn Asp Thr Glu Leu Val Ala Cys Leu
290                 295                 300
Arg Thr Arg Pro Ala Gln Val Leu Val Asn His Glu Trp His Val Leu
305                 310                 315                 320
Pro Gln Glu Ser Val Phe Arg Phe Ser Phe Val Pro Val Val Asp Gly
            325                 330                 335
Asp Phe Leu Ser Asp Thr Pro Glu Ala Leu Ile Asn Ala Gly Asp Phe
            340                 345                 350
His Gly Leu Gln Val Leu Val Gly Val Val Lys Asp Glu Gly Ser Tyr
            355                 360                 365
Phe Leu Val Tyr Gly Ala Pro Gly Phe Ser Lys Asp Asn Glu Ser Leu
        370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
            405                 410                 415
Leu His Pro Glu Asp Pro Ala Arg Leu Arg Glu Ala Leu Ser Asp Val
            420                 425                 430
Val Gly Asp His Asn Val Val Cys Pro Val Ala Gln Leu Ala Gly Arg
        435                 440                 445
Leu Ala Ala Gln Gly Ala Arg Val Tyr Ala Tyr Val Phe Glu His Arg
450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
            485                 490                 495
Thr Ala Glu Glu Lys Ile Phe Ala Gln Arg Leu Met Arg Tyr Trp Ala
            500                 505                 510
Asn Phe Ala Arg Thr Gly Asp Pro Asn Glu Pro Arg Asp Pro Lys Ala
            515                 520                 525
Pro Gln Trp Pro Pro Tyr Thr Ala Gly Ala Gln Gln Tyr Val Ser Leu
        530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Gly Met
            565                 570                 575
Gln Gly Pro Ala Gly Ser Gly Trp Glu Gly Ser Gly Ser Pro Pro
            580                 585                 590
Gly Val Thr Pro Leu Phe Ser Pro
        595                 600

(2) INFORMATION FOR SEQ ID NO:2:

(i) SEQUENCE CHARACTERISTICS:
        (A) LENGTH: 25 amino acids
        (B) TYPE: amino acid
        (C) STRANDEDNESS: single
        (D) TOPOLOGY: linear
```

(ii) MOLECULE TYPE: peptide (iii) HYPOTHETICAL: NO (iv) ANTI-SENSE: NO (xi) SEQUENCE DESCRIPTION: SEQ ID NO:2:

Gly Met Gln Gly Pro Ala Gly Ser Gly Trp Glu Glu Gly Ser Gly Ser
1               5                   10                  15

Pro Pro Gly Val Thr Pro Leu Phe Ser
            20                  25

(2) INFORMATION FOR SEQ ID NO:3:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Leu Leu Ser Ala Thr Gly Met Gln Gly Pro Ala Gly Ser Gly Trp Glu
1               5                   10                  15

Glu Gly Ser Gly Ser Pro Pro Gly Val Thr Pro Leu Phe Ser Pro
            20                  25                  30

(2) INFORMATION FOR SEQ ID NO:4:

(i) SEQUENCE CHARACTERISTICS:
            (A) LENGTH: 48 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Leu Leu Ser Ala Thr Ala Ser Glu Ala Pro Ser Thr Cys Pro Gly Phe
1               5                   10                  15

Thr His Gly Glu Ala Ala Pro Arg Pro Gly Leu Pro Leu Pro Leu Leu
            20                  25                  30

Leu Leu His Cys Leu Leu Leu Leu Phe Leu Ser His Leu Arg Arg Leu
            35                  40                  45

(2) INFORMATION FOR SEQ ID NO:5:

(i) SEQUENCE CHARACTERISTICS:
            (A) LENGTH: 45 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

```
Leu Leu Ser Ala Thr Asp Thr Leu Asp Glu Ala Glu Arg Gln Trp Lys
1               5                   10                  15

Ala Glu Phe His Arg Trp Ser Ser Tyr Met Val His Trp Lys Asn Gln
                20                  25                  30

Phe Asp His Tyr Ser Lys Gln Asp Arg Cys Ser Asp Leu
            35                  40                  45
```

(2) INFORMATION FOR SEQ ID NO:6:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Primer"

(iii) HYPOTHETICAL: NO (iv) ANTI-SENSE: NO (xi) SEQUENCE DESCRIPTION: SEQ ID NO:6:

TCTTATTCCG TTCCCTTCGG ATTCTCCGTT  30

(2) INFORMATION FOR SEQ ID NO:7:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Primer"

(iii) HYPOTHETICAL: NO (iv) ANTI-SENSE: NO (xi) SEQUENCE DESCRIPTION: SEQ ID NO:7:

TCTTATTCCG TTCCCTTCGG ATTCTCCGTT  30

(2) INFORMATION FOR SEQ ID NO:8:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Primer"

(iii) HYPOTHETICAL: NO (iv) ANTI-SENSE: NO (xi) SEQUENCE DESCRIPTION: SEQ ID NO:8:

AGACTGCCTG TATCTTAATG TGTGGACACC  30

(2) INFORMATION FOR SEQ ID NO:9:

(i) SEQUENCE CHARACTERISTICS:
  (A) LENGTH: 30 base pairs
  (B) TYPE: nucleic acid
  (C) STRANDEDNESS: single
  (D) TOPOLOGY: linear -continued

```
  (ii) MOLECULE TYPE: other nucleic acid
       (A) DESCRIPTION: /desc = "Primer"

(iii) HYPOTHETICAL: NO (iv) ANTI-SENSE: NO (xi) SEQUENCE DESCRIPTION: SEQ ID NO:9:

CGGCTGATGA GAGATTCATT GTCTTTGCTG                                          30
```

METHOD AND COMPOSITION FOR ENABLING PASSAGE THROUGH THE BLOOD-BRAIN-BARRIER

CROSS REFERENCE TO RELATED APPLICATIONS

This application claims priority from U.S. Provisional Applications 60/031,194 filed Nov. 20, 1996, 60/035,266 filed Dec. 12, 1996 and 60/053,200 filed Jul. 21, 1997.

GOVERNMENT SUPPORT

Research in this application was supported in part by U.S. Department of the Army Contract DAMD17-86-C-6010. The U.S. Government has a nonexclusive, nontransferable, irrevocable paid-up license to practice or have practiced this invention for or on its behalf as provided by the terms of Contract DAMD17-86-C-6010 awarded by the U.S. Department of the Army.

BACKGROUND OF THE INVENTION

1. Field of the Invention

The present invention relates to a method and composition for transporting compounds including pharmaceutical compositions across the Blood-Brain Barrier (BBB).

2. Description of Related Art

The Blood-Brain Barrier (BBB) maintains a homeostatic environment in the central nervous system (CNS). The capillaries that supply the blood to the brain have tight junctions which block passage of most molecules through the capillary endothelial membranes. While the membranes do allow passage of lipid soluble materials, such as heroin and other psychoactive drugs, water soluble materials such as glucose, proteins and amino acids do not pass through the BBB. Mediated transport mechanisms exist to transport glucose and essential amino acids across the BBB. Active transport mechanisms remove molecules which become in excess, such as potassium, from the brain. For a general review see Goldstein and Betz, 1986 and Betz et al, 1994, incorporated herein in their entirety by reference.

The BBB was initially observed by Ehrlich when he observed what he termed "lower affinity" of vital dyes for the brain than other tissue. Goldmann in 1913 however, determined the actual presence of a barrier by showing that the vital dye trypan blue when injected directly into the brain stained the brain but did not leave the CNS. These early experiments by Golmann and others established that the CNS is separated from the bloodstream by blood-brain and blood-cerebrospinal fluid (CSF) barriers.

The BBB impedes the delivery of drugs to the CNS. Methods have been designed to deliver needed drugs such as direct delivery within the CNS by intrathecal delivery can be used with, for example, an Ommaya reservoir. U.S. Pat. No. 5,455,044 provides for use of a dispersion system for CNS delivery or see U.S. Pat. No. 5,558,852 for a discussion of other CNS delivery mechanisms as well as Betz et al [1994] and Goldstein and Betz [1986].

There has been some progress in designing drugs that utilize the structure and function of the BBB itself to deliver the drugs. These drugs are designed to be lipid soluble or to be "piggy-backed" into the CNS by being coupled to peptides that can cross the BBB through mediated transport mechanisms. However, not all drugs are amenable to this solution. Partridge and his colleagues have worked extensively in this area. Pharmacological formulations that cross the blood-brain barrier can be administered. [Brem et al., 1993] Such formulations can take advantage of methods now available to produce chimeric peptides in which the present invention is coupled to a brain transport vector allowing transportation of these engineered drugs across the barrier [Pardridge, et al., 1992; Pardridge, 1992; Bickel, et al., 1993]. See also The Exonomist, Jan. 4, 1997.

In the disease process, the BBB is often disrupted. For example in meningitis, Tuomanen [1993] has shown that the response against the bacterial infection lead to a breach of the BBB. Further, in trauma and brain tumors the BBB is often disrupted as well as exposure to certain agents such as soman [Lallement et al, 1991; Petrali et al, 1991]. Disruption has been shown in ischemia [Burst, 1991] and in Alzheimer's Disease [Harik and Kalaria, 1991].

In appropriate cases the blood-brain barrier disruption can be utilized to deliver drugs to the CNS, as for example osmotic disruption [Neuwelt et al., 1980a]. However, generally this is not the case since, for example, exposure to soman is accompanied by seizures [Petrali et al, 1991].

However, while these methods do provide CNS delivery for some drugs it would be useful to have additional means of delivery. In particular it would be useful to have mechanisms that temporarily and reversibly open the BBB to allow non-engineered drugs through.

Stress has been shown to affect the permeability of the BBB [Sharma, et al, 1991; Ben-Nathan, et al, 1991]. Further, in mammals, acute stress elicits a rapid, transient increase in released acetylcholine (ACh) with a corresponding phase of increased neuronal excitability [Imperato, et al, 1991]. There have been some studies showing that the pharmacological blockade of acetylcholine—hydrolyzing enzyme, acetylcholine esterase (AChE) promotes a similar enhancement in electrical activity in cortical neurons [Ennis and Shipley, 1992].

AChE has three splice variant AChEmRNAs (FIG. 1). Alternative splicing controls the generation of proteins with diverse properties from single genes through the alternate excision of intronic sequences from the nuclear precursors of the relevant mRNAs (Pre-mRNA). It is known to be cell type-, tissue- and/or developmental stage-specific and is considered as the principal mechanism controlling the site(s) and timing of expression and the properties of the resultant protein products from various genes.

Three alternative AChE-encoding mRNAs have been described in mammals (FIG. 1). The dominant brain and muscle AChE (AChE-T) is encoded by an mRNA carrying exon E1 and the invariant coding exons E2, E3, and E4 spliced to alternative exon E6. AChEmRNA bearing exons E1–4 and alternative exon E5 encodes the glycolipid phosphatidylinositol (GPI)-linked form of AChE characteristic of vertebrate erythrocytes (AChE-H). An additional readthrough mRNA (AChE-I4) species (Table 1, SEQ ID No:1) retaining the intronic sequence I4 (SEQ ID No:2; FIG. 2) located immediately 3' to exon E4 is found in rodent bone marrow and erythroleukemic cells and in various tumor cells lines of human origin. (The book *Human Cholinesterases and Anticholinesterases* by Soreq and Zakut (Academic Press, Inc., 1993) provides a summation of the biochemical and biological background as well as the molecular biology of human cholinesterase genes and the proteins. The book in its entirety is incorporated herein by reference.)

It would be useful to facilitate transport through the BBB by using a stress mimicking agent to have a controlled reversible disruption, or opening, of the BBB and/or blood-CSF.

SUMMARY OF THE INVENTION

According to the present invention, a pharmaceutical composition for facilitating passage of compounds through the blood-brain barrier comprising the ACHE-I4 readthrough (SEQ ID No:1) splice variant or the I4 peptide (SEQ ID No:2) and analogues of each thereof and a pharmaceutically acceptable carrier is disclosed. Alternatively, the pharmaceutical composition for facilitating passage of compounds through the blood-brain barrier can comprise adrenaline, atropine and dopamine and a combination of dopamine and propanolol and a pharmaceutically acceptable carrier. Combinations of these agents can also be used.

The composition of the present invention can optionally include the compound to be transported across the BBB. Alternatively, the compound can be co-administered (simultaneously) with the composition or can be administered at some point during the biologically effective period of the action of the composition. That is the composition facilitates disruption of the BBB, i.e. opens the BBB, for a period depending on the dose and the compound can be administered during this relevant period.

The present invention provides a method for administering a compound to the CNS of an animal by subjecting the animal to a stress-mimicking agent or treatment. This agent or treatment facilitates disruption of the blood-brain barrier. During the period that the BBB is opened or disrupted a compound can be administer such that the compound is enabled to passage through the disrupted BBB into the CNS.

The method and composition of the present invention therefore provides for delivery to the central nervous system of compounds that are necessary for treatment modalities in any condition affecting the central nervous system where the blood-brain barrier would impede the delivery of the compound. These conditions can include any disease or pathology of the central nervous system and can include neuropsychiatric disorders. The method and composition of the present invention is an improvement of currently available means of delivery of compounds to the central nervous system through the blood-brain barrier.

DESCRIPTION OF THE DRAWINGS

Other advantages of the present invention will be readily appreciated as the same becomes better understood by reference to the following detailed description when considered in connection with the accompanying drawings wherein:

FIGS. 3A–B show that acute stress and anticholinesterases modulate CNS gene expression similarly. FIG. 3A are photographs showing RT-PCR analysis, C-fos RT-PCR traces represent mRNA preparations from 10 minute post-treatment, ACHE, synaptophysin and ChAT products represent RNA preparations from 30 minute following either stress or AChE inhibition. One out of 6 reproducible in vivo and in vitro experiments is shown. FIG. 3B are extracellular evoked potentials recordings of stratum oriens fibers using glass microelectrodes in the CA1 area before (Control) or 30 minutes following addition of 1 $\mu$M DFP (Anti-AChE), to the perfusing solution. Note the increased amplitude and duration of evoked extracellular field potentials and the enhanced paired-pulse facilitation. One out of 5 experiments showing AChE inhibition promotes neuronal excitability.

FIGS. 4A–D show delayed suppression of the hyperexcitation evoked by AChE inhibition. Graphs at (A) One hour administration of 1 or 10 uM carbachol, (B) average and standard deviation values for 6 measurements per point of population spikes evoked in response to the noted stimulus intensities in hippocampal slices under control conditions (control, empty circles), or following 1 or 3 hours under continuous perfusion of 10 $\mu$M physostigmine (filled circles or squares, respectively), (C) graphs show population spike traces from slices under 1 hour control conditions (cont.), following 1 hour under co-exposure to 1 uM physostigmine and 1 uM atropine (phy+at), or 1 hour after that, when atropine was washed off and under continued exposure to physostigmine, Note the absence of excitation response under atropine and that no suppression took place 1 hour after its removal. FIG. 4D are traces of Paired-pulse facilitation enhancement with first and second responses (V1, V2) separated by a 500 msec interval or the difference between such responses (V2–V1) following 50, 100 or 500 msec intervals for hippocampal slices under control conditions or following 1 or 3 hours of perfusion with 1 mM physostigmine. Note the prolonged duration and the intense signals of facilitation responses recorded 1 hour following physostigmine addition to the perfusion medium and the suppression of both these responses after 3 hours of such exposure.

FIGS. 5A–B show that physiological and transcriptional responses both depend on intracellular Ca++ mobilization and Na+ influx. FIG. 5A is a graph showing prevention of facilitation enhancement.: Duration of paired-pulse facilitation responses was measured as in FIG. 4C in hippocampal slices under control conditions (empty triangles), 1 hour following the addition of 1 uM pyridostigmine to the perfusion medium (full squares) or 1 hour following treatment with both 1 uM physostigmine and 1 uM BAPTA-AM (full triangles). Note the complete prevention of the physostigmine-induced prolongation of paired-pulse facilitation under BAPTA-AM. FIG. 5B are photographs showing suppression of the transcriptional response: c-fos, ChAT and synaptophysin mRNAs were PCR-amplified as in FIG. 3A from control slices (cont.) or slices treated for 1 hour with 1 mM pyridostigmine (Pyr) alone, or with pyridostigmine and 1 uM of the Ca++ chelator BAPTA-AM or the Na+ channel blocker tetrodotoxin (TTX). Note that the anticholinesterase-induced changes in c-fos and ChAT mRNA were both suppressed by either BAPTA-AM or TTX, demonstrating that these transcriptional changes depend both on the increased intracellular Ca2+ and on Na+ influx.

FIG. 6A graph shows specific AChE activities in $\mu$mole acetylthiocholine (ATCh) hydrolyzed per hour per mg tissue spectrophotometrically determined in extracts of cortex, cerebellum or hippocampus prepared from animals sacrificed at the noted times after forced swimming protocol. Presented are percent of control activities for each brain region for 10 out of 20 studied mice. FIG. 6B is a photograph showing stress intensifies cortical AChE activity and diversifies its electrophoretic heterogeneity. Cortical protein extracts were electrophoresed (20 ul per lane, 1:10 w/vol) in 7% non-denaturing polyacrylamide gels. Gels were histochemically stained for catalytically active AChE. Note the post-stress increase in activity and the electrophoretic heterogeneity of cortical AChE following stress. One of 10 experiments.

FIGS. 7A–B shows selective induction of readthrough AChEmRNA following stress and AChE inhibition. FIG. 7A are photographs showing kinetic follow-up of RT-PCR: Positions of primer pairs specific for the alternatively spliced AChEmRNA subtypes are presented on the left. [Primer pair 1361+/1869– ("E6") detects mRNA encoding the synaptic AChE form; 136.1+/175– ("I4/E5") detects both a 549 bp product of readthrough AChEmRNA and a 432 bp product encoding the GPI-lined red blood cell (RBC) form of the enzyme]. Note that both in vivo stress and in vitro AChE inhibition promoted significant increases of the readthrough (I4) but not the synaptic (E6) or erythrocyte (E5) forms of AChEmRNA. The bands displayed in the top right hand panel represent endpoint PCR products from a reaction using a nested readthrough AChEmRNA primer pair (1361+/74–) detected by hybridization with a radiolabelled probe. FIG. 7B are photographs showing the result of in situ hybridization: 5 uM thick paraffin-embedded cortical slices were incubated with 50-mer 5'-biotinylated, chemically protected complementary RNA probe directed against exon 6 initiated at nt.1869 (left), or intron I4 initiated at position 74 (right), of the mouse AChE gene. Signals were detected using alkaline phosphatase-streptavidin conjugates and Fast Red as a substrate. Shown are cortical layers II–V (upper panels), and magnified pyramidal neurons of cortical layer no. 2 (lower panels). Note that I4 labeling was essentially limited to layers II+V under control conditions, but was intensified and included layer III+IV after exposure to AChE inhibitor (pyridostigmine, 2 mg/kg). Also, the subcellular localization of I4-AChEmRNA shifted from around the nucleus under control conditions to the entire cell bodies and their apical dendrites following AChE inhibition.

FIGS. 10A–B: Pyridostigmine enhances neuronal excitability and increases oncogene mRNA levels. A: The kinetics of brain c-fos and AchE mRNA accumulation during RT-PCR amplification. RNA was extracted and reverse transcribed as under FIG. 9. The earlier appearance of the amplified PCR product 20 minutes following injection of 2 mg/kg pyridostigmine (+) as compared to 0.9% NaCl (–) indicates an increase in the amount of c-fos (upper panel) and AChE mRNA (lower panel) under pyridostigmine exposure. B: Extracellular evoked potentials. Cortico-hippocampal slices (400 mm thick) were cut using a vibratome (Vibroslice, Campden Instruments, Loughborough, UK.), and were placed in a humidified holding chamber, continuously perfused with oxygenated (95% O2, 5% CO2) artificial cerebrospinal fluid (aCSF) [Blick et al, 1994]. Schaffer collateral fibers were stimulated with a bipolar tungsten stimulating electrode and extracellular evoked potentials were recorded in the cell-body layer of the CA1 area of the hippocampus. Single response to supramaximal stimulus intensity (1.5 times stimulus the intensity of which caused maximal response) is drawn before (–) and 30 minutes following (+) addition of pyridostigmine (1 mM) to the perfusing solution.

FIGS. 14A–B shows the diffusion of horseradish peroxidase into brains following disruption of the BBB wherein (A) is a diagrammatic representation of the brain and areas evaluated for dye concentration and (B) are photomicrographs of this regions in control non-stressed (cont.) and stress animals.

DETAILED DESCRIPTION OF THE INVENTION

Figure 1:
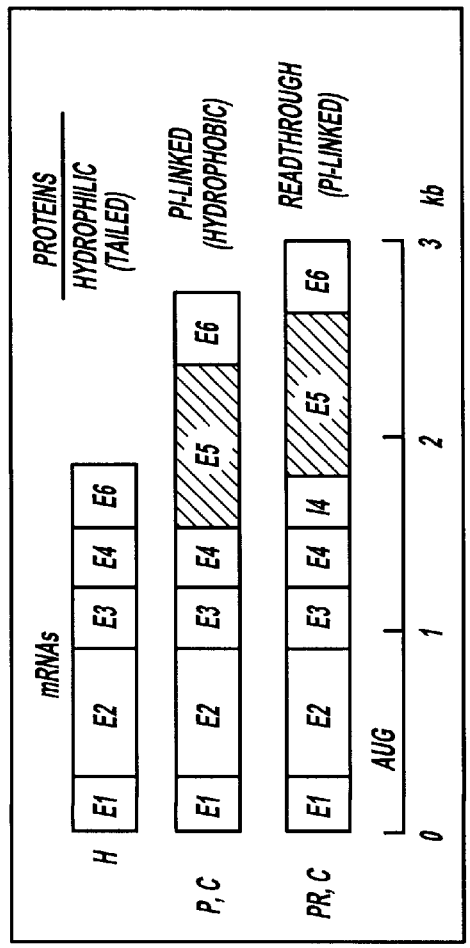
FIG. 1 is a schematic diagram of the three splice variants of AChE.
Figure 2:
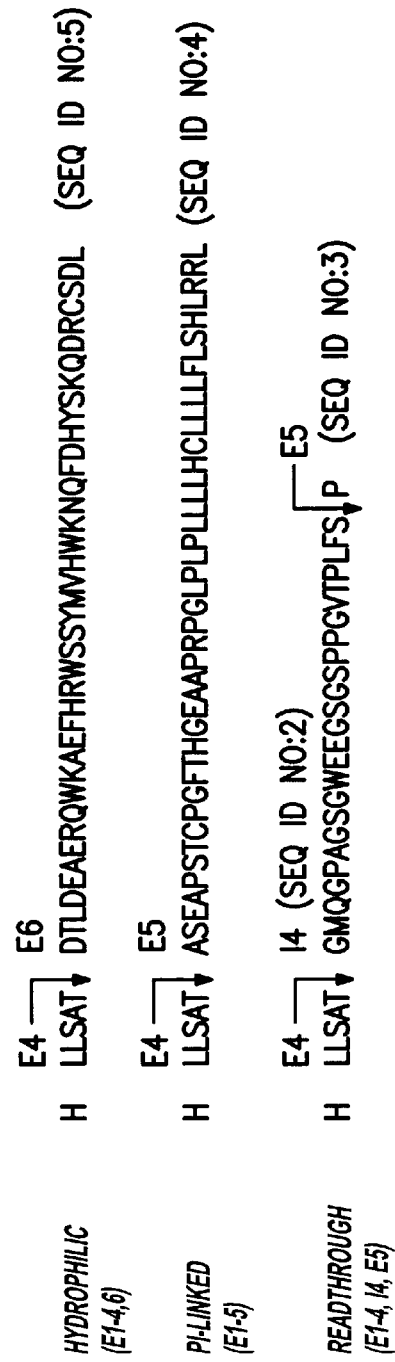
FIG. 2 is shows the amino acid sequences of human (H) AChE variants from the end of E4 to the end of the protein in the three variants, E1–4,6 (SEQ ID No:3), E1–5 (SEQ ID No:4), E1-4-I4-E5 (readthrough; SEQ ID No:5).

The present invention provides a pharmaceutical composition with agents for facilitating passage of compounds through the blood-brain barrier (BBB) into the central nervous system (CNS). As used herein the term BBB also encompasses the blood-CSF barrier. The composition comprises an effective amount of the AChE-I4 readthrough (SEQ ID No:1) splice variant protein and a pharmaceutically acceptable carrier. Alternatively the composition comprises an effective amount of the I4 peptide (SEQ ID No:2) and a pharmaceutically acceptable carrier. The composition can also comprise an effective amount of at least one of dopamine (DA), atropine and/or adrenalin and a pharmaceutically acceptable carrier. Further, the agent can be a combination of an α adrenergic agonist and β adrenergic antagonist referred to herein after as an adrenergic combination agent such as dopamine and propanolol. Combinations of these agents can be used. These compositions facilitate a reversible disruption (opening) of the BBB allowing transport of compounds through the BBB.

Analogues with the same biological activity as SEQ ID Nos:1–2 can be used in the pharmaceutical composition of the present invention. The term analogue as used herein is defined as a variant amino acid sequence alteration, with some differences in their amino acid sequences as compared to the native sequence of SEQ ID Nos:1–2. The amino acid sequence of an analog may differ from that of the SEQ ID Nos:1–2 when at least one residue is deleted, inserted or substituted, but the protein and/or peptide retains its biological activity with respect to the present invention.

The amount administered is determined as shown in the examples herein, generally by dye exclusion tests, calibrated to show the amount necessary to open or disrupt the BBB and the duration of the disruption. CT scans in particular as shown in Example 5 are particularly useful in establishing the amount administered as is the method disclosed in Example 6. These amounts are determined on a species basis and are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve a reversible disruption of the BBB. In general the amounts used in Examples 2 and 6 can be used with the appropriate conversion to human dosages as is known in the art.

The composition of the present invention can optionally include the compound to be transported across the BBB. Alternatively, the compound can be co-administered (simultaneously) with the composition or can be administered at some point during the biologically effective period of the action of the composition. That is the composition facilitates disruption of the BBB, i.e. opens the BBB, for a period depending on the dose and the compound can be administered during this relevant period.

The compounds are used for diagnostic or treatment modalities in any condition affecting the central nervous system where the blood-brain barrier would impede the delivery of the compound. For example, the composition of the present invention can be used to deliver contrast agents (dyes) that are needed for imaging of the CNS. These conditions can include any disease or pathology. They can include, but are not limited to, infections, neurochemical disorders, brain tumors and gliomas, demyelination, other neuropathies, encephalopathies, coma, ischemia, hypoxia, epilepsy, dementias, cognitive disorders, neuropsychiatric disorders (including depression, anxiety, schizophrenia and the like) as well as genetic disorders. The compounds to be administered can range from antibiotics to chemotherapeutic drugs to vectors to be used for gene therapy. The compounds can include agents that can be used to block the effects of abused drugs. These compounds are administered and dosed as is known in the art for these compounds in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The compound can be administered in various ways which are selected to deliver the compound to the BBB at the appropriate time when the barrier has been disrupted or opened to facilitate transport through the BBB into the CNS. The patient being treated is a warm-blooded animal and, in particular, mammals including man. It is noted that humans are treated generally longer than the mice or other experimental animals exemplified herein which treatment has a length proportional to the length of the disease process and drug effectiveness and body size and metabolism.

The present invention provides a pharmaceutical composition for facilitated administration of a compound or drug through the blood-brain barrier. The compound or drug is given in combination with an inducing means for mimicking stress and a pharmaceutically acceptable carrier. The inducing means can include either administering a stress-mimicking agent or applying a stress-mimicking inducing treatment.

A stress-mimicking inducing treatment is hypnosis [Solomon et al, 1992; Spiegel, 1992; Putnam, 1992]. The use of hypnosis allows the recalling of stressful events in a controlled environment. The recall of the stressful events generates the release of AChE-I4 in the brain thereby generating in situ a disruption of the BBB. The timing of the administration of the compound is timed to coincide with the window of time of relived stress.

Stress-mimicking agents such as dopamine, adrenaline and/or atropine can be used as shown herein in the examples. For example, adrenaline is released in stress, therefore its administration mimics a stress. Stress-mimicking agents such as ACHE-I4 (SEQ ID No:1) or I4 peptide (SEQ ID No:2) can also be used since they are also released in response to stress and therefore their administration mimics a stress. An adrenergic combination agent consisting of an α adrenergic agonist and β adrenergic antagonist can also be used such as dopamine and propanolol respectively. Combinations of these stress mimicking agents can also be used.

The amount administered is determined as shown in the examples herein, generally by dye exclusion tests, calibrated to show the amount necessary to open or disrupt the BBB and the duration of the disruption. CT scans can be used for the calibration as can the method set forth in Example 6. These amounts are determined on a species basis and are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve a reversible disruption of the BBB.

The present invention provides a method for administering a compound to the CNS of an animal by subjecting the animal to a stress-mimicking agent or treatment. This agent or treatment facilitates disruption of the blood-brain barrier. During the period that the BBB is opened or disrupted a compound can be administer such that the compound is enabled to passage through the disrupted BBB into the CNS.

A stress-inducing treatment is hypnosis [Solomon et al, 1992; Spiegel, 1992; Putnam, 1992] as described herein above. Stress inducing agents such as adrenaline, atropine, dopamine and adrenergic combination agents can be used as shown herein in the examples. Stress mimicking agents such as ACHE-I4 (SEQ ID No:1) or I4 peptide (SEQ ID No:2) can be used. These agents can be used in combination.

The administration of the compound can be simultaneous with subjecting the patient to a means of inducing stress (treatments and/or agents). Alternatively, the compound can be administered during the time period when the BBB is reversibly open.

In Example 1, BBB permeability in response to stress is shown in mice and humans utilizing pyridostigmine brain penetration studies. Pyridostigmine, a carbamate acetylcholinesterase (AChE) inhibitor, is routinely employed in the treatment of the autoimmune disease myasthenia gravis [Taylor, 1990]. Pyridostigmine is also recommended by most western armies for use as pretreatment under threat of chemical warfare, because of its protective effect against organophosphate poisoning [Deyi et al, 1981; Diruhumber et al, 1979]. Due to this drug's quaternary ammonium group, which prevents its penetration through the blood-brain-barrier (BBB), the symptoms associated with its routine use primarily reflect perturbations in peripheral nervous system functions [Taylor et al, 1990; Borland et al, 1985]. Unexpectedly, under similar regimen, pyridostigmine administration during the Gulf War resulted in an >3 fold increase in the frequency of reported central nervous system symptoms [Sharabi et al, 1991]. This was not due do enhanced absorption (or decreased elimination) of the drug because the inhibition efficacy of serum butyrylcholinesterase was not modified [Sharabi et al, 1991].

In Example 2 BBB permeability to Evans Blue dye following stress or the administration of adrenaline or atropine is shown. These results show that adrenaline or atropine can, at physiologically meaningful doses, provide increased permeability of the BBB. This study is further explored in Example 4 where the BBB permeability to Horseradish peroxidase is studied and more detailed neuroanatomical detail is determined. In Example 6, adrenergic manipulation of the BBB permeability is disclosed, showing that simultaneous activation of α adrenergic receptors together with blockade of β adrenergic receptors effects a synergistic effect on BBB permeability/disruption.

In Example 3 pronounced reductions in choline acetyltransferase and vesicular acetylcholine transporter mRNAs accompanied prolonged increases in a rare acetylcholinesterase variant (readthrough AchE-I4) in acutely stressed mice and in anticholinesterase-treated mice and hippocampal brain slices. These calcium-dependent modulations in gene expression coincided with transient enhancement and delayed depression phases of neuronal excitability, both mediated by acute cholinergic stimulation. Our findings implicate concerted cholinergic feedback mechanisms in parallel long-term responses to stress and exposure to anticholinesterases.

In Example 5 Computerized Tomography (CT) was used to measure the amount of disruption of the BBB and to correlate this disruption with CSF protein content and cholinergic activity.

The above discussion provides a factual basis for the use of stress-mimicking compounds or treatments to facilitate disruption of the BBB to delivery compounds to the CNS. The methods used with and the utility of the present invention can be shown by the following non-limiting examples and accompanying figures.

EXAMPLES

General Methods

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.) Reactions and manipulations involving other nucleic acid techniques, unless stated otherwise, were performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference.

Stress Induction: Stress was induced in adult FVB/N mice by 2×4 minute forced swim with a 4 minute rest interval in a 60×60 cm water bath at about 21° C., adapted from Melia et al, [1994]. Ten minutes following stress-induction animals were injected i.p. with 0.9% NaCl (control), pyridostigmine (Research Biochemical International, Natik, Mass.) or physostigmine (Sigma, St Louis, Mich.) at the indicated doses. Animals were decapitated 10 minutes following injection, trunk blood was collected [Melia et al, 1994], and cerebral cortex was quickly dissected and homogenized in solution D (10 mM Tris-HCl, pH 7.4, 1M NaCl, 1% Triton-X100, 1 mM EDTA, 1:10 weight/volume)[Neville et al, 1990]

AChE activity measurements: Acetylthiocholine (ATCh) hydrolysis levels were determined spectrophotometrically in nmol ATCh per minute per mg brain protein, as previously described [Seidman et al, 1995]. BuChE activity in serum was measured using Butyrylthiocholine (BTCh) as substrate. In both cases, selective inhibitors were employed to suppress non-specific hydrolysis [Neville et al, 1990].

Determination of Blood-Brain-Barrier permeability: Evan's Blue: Anaesthetized animals (Nembutal, 60 mg/kg), were injected intracardially with 0.1 ml of 2% of the albumin-binding dye Evan's-blue in 0.9% NaCl. Following perfusion with 0.9% NaCl, brains were removed, homogenized and dye concentration determined spectrophotometrically [Uyama et al, 1988]. Plasmid DNA: 100 ug of plasmid CMVACHE DNA (ca. 6 Kb) in 0.1 ml of 0.9% of NaCl was injected i.p. into control or stressed animals. Animals were sacrificed 20 minutes following injection, trunk blood and brain were collected and plasmid DNA detected by kinetic follow-up of PCR amplification in tissue homogenates treated with proteinase K (100 (g/ml, overnight incubation, 65° C.).

RT-PCR: Brain c-fos cDNA was amplified by RT-PCR using as primers 1604(+): 5'TCTTATTCCGTTCCCTTCG-GATTCTCCGTT3' (SEQ ID No;6) and 2306(−): 5'TCT-TATTCCGTTCCCTTCGGATTCTCCGTT3' (SEQ ID No:7). Brain AChE cDNA was amplified using as primers 375(+): 5'AGACTGCCTGTATCTTAATGTGTGGACACC 3' (SEQ ID No:8) and1160(−): 5' CGGCTGATGAGAGAT-TCATTGTCTTTGCTG 3' (SEQ ID No:9). Numbers. denote nucleotide positions in the Genebank c-fos sequence (accession no. V00727), or in the mouse AChE cDNA sequence [Rachinsky et al, 1990] respectively. Ten ml of each reaction mixture, were removed every third cycle from 18 to 39, electrophoresed and stained with ethidium bromide [Seidman et al, 1995].

Electrophysiological Recordings: Extracellular potentials were recorded in hippocampal slices maintained in vitro [Friedman and Gutnick, 1989]. Schaffer collateral fibers were stimulated with a bipolar tungsten stimulating electrode. Recording glass microelectrodes were located in the CA1 area.

EXAMPLE 1

In this Example a forced swim protocol, shown previously to induce stress [Melia et al, 1994], gives an increase in BBB permeability and reduces by >100 fold the pyridostigmine dose required to inhibit mouse brain AChE activity by 50%. Under these conditions, peripherally administered pyridostigmine increased the brain levels of c-fos oncogene and AChE mRNAs. Moreover, in-vitro exposure to pyridostigmine increased both electrical excitability and c-fos mRNA levels in brain slices, demonstrated that the observed changes could be directly induced by pyridostigmine. These findings demonstrate that peripherally acting drugs administered under stress may reach the brain and affect centrally controlled functions.

Figure 9:
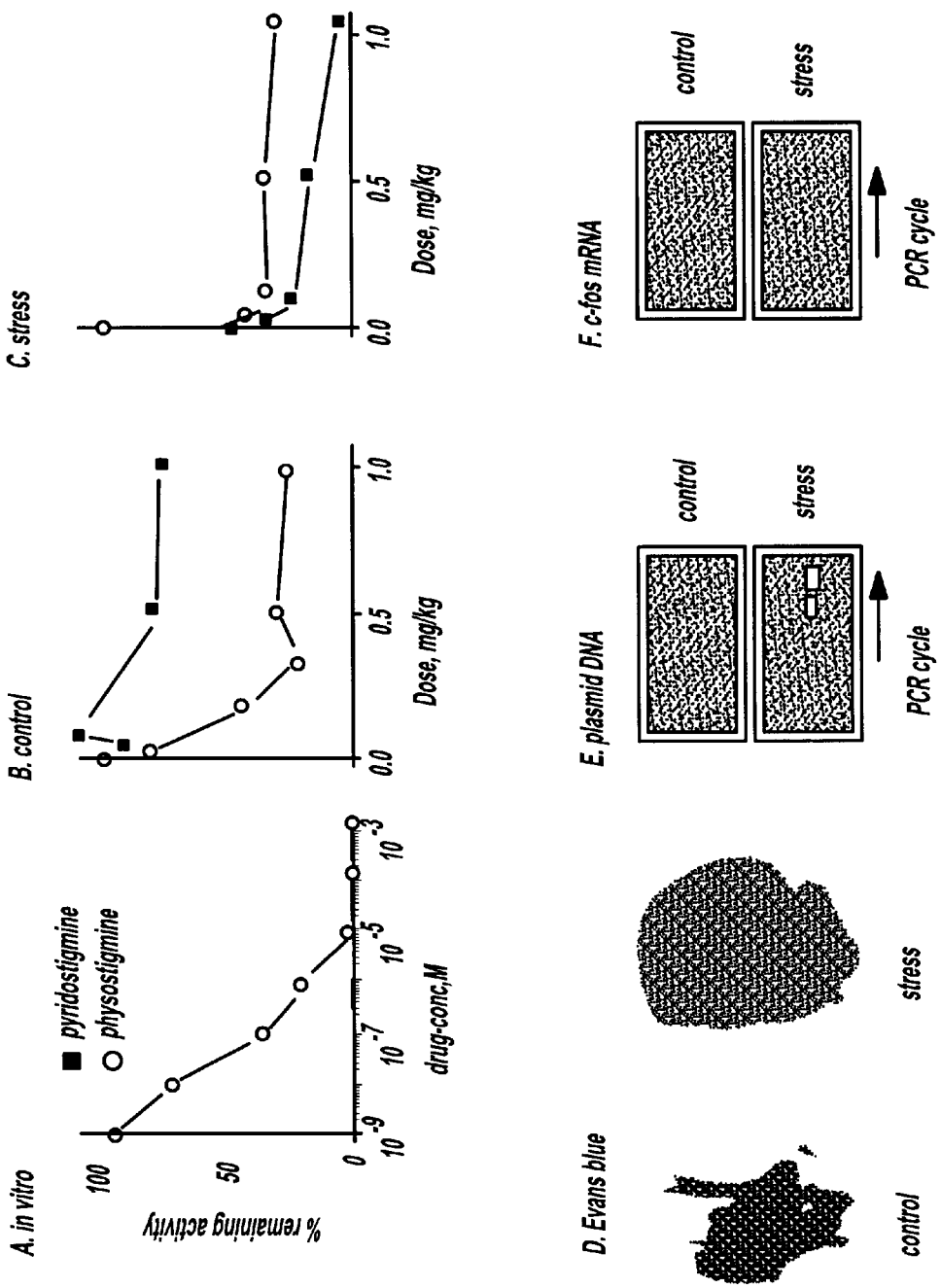
FIGS. 9A–F demonstrates that stress intensifies AChE inhibition by pyridostigmine due to increased brain penetration. A: AChE inhibition in brain homogenates. Acetylthiocholine hydrolysis was measured following addition of increasing concentrations of pyridostigmine (filled squares) or physostigmine (empty circles) to brain homogenates from control animals. Presented are percent remaining activities as compared with those of brain homogenates with no added drug. B: Inhibiting brain AChE activity by drug injection. Percent of normal specific cortical AChE activity was measured in brain homogenates prepared from non-stressed animals sacrificed 10 minutes following injection of the noted doses of physostigmine (n=9) or pyridostigmine (n=11). Presented are percent remaining activities as compared with those of brain homogenates from non-stressed, 0.9% NaCl injected animals (n=12). C: Pyridostigmine inhibition of brain AChE following stress. Swim forced test was followed 10 minutes later by injection of either 0.1 mg/kg pyridostigmine (n=8), or physostigmine (n=5). AChE activity measurements were as under B. Presented are percent remaining activities as compared with those of brain homogenates from similarly stressed, 0.9% NaCl injected animals (n=6). D: BBB permeability following stress. Shown are representative brains dissected from anaesthetized animals, 10 minutes following intracardial injection of Evan's-blue. Control: non-stressed animal, stress: 10 minutes following stress session. E: Plasmid DNA penetration to the brain under stress. Control and stressed animals were injected i.p. with CMVACHE [Ben Aziz-Aloya, et al, 1993] plasmid. Proteinase K-treated -brain homogenates were subjected to PCR amplification using a set of CMV-promoter forward primer and an ACHE reverse primer. PCR product samples were withdrawn every third cycle, which allows for 8-fold increases between samples. CMVACHE DNA was detected starting from cycle 21 in the brain of 4 out of 4 stressed animals. The PCR products from brain of control animals were considerably weaker and appeared only on cycle 24, indicating at least 8-fold less plasmid DNA in control brains as compared to stressed ones. In 2 out of 5 control animals no PCR product was detected. F: Kinetics of brain c-fos cDNA accumulation during RT-PCR amplification. Total RNA from mouse hippocampus was extracted using RNAclean (AGS,Heidelberg,Germany), its integrity verified by gel electrophoresis (evaluation of 2.0 ratio between 28 S and 18 S ribosomal RNA) and its quantity and purity from protein contamination evaluated by a A260/A280 ratio of 1.8–2.0. c-fos cDNA was amplified following reverse transcription of equal amounts of total RNA samples from the brain of control or stressed animals. Kinetic follow-up of product accumulation was carried out as under E. The earlier appearance of amplified c-fos cDNA, 20 minutes following stress session as compared to control, indicates a significant increase in the amount of c-fos mRNA under stress.

Pyridostigmine and physostigmine displayed similar efficacy in inhibiting AChE activity when added to brain homogenates (FIG. 9A). Also, they were similarly effective in reducing serum butyrylcholinesterase (BuChE) activity when injected intraperitoneally (i.p.) into non-stressed mice (16.7+/−6.9% and 22.6+/−5.4% reduction from normal levels respectively, 10 minutes following injection of 0.1 mg/kg pyridostigmine or physostigmine into 3 animals in each group). However, brain AChE activity in homogenates prepared from non-stressed mice was considerably less inhibited by the injected pyridostigmine than by physostigmine (FIG. 9B). Thus, pyridostigmine doses previously proven to be protective against organophosphates (0.1–0.5 mg/kg, 15–30% inhibition of serum BuChE activity) [Deyi et al, 1981; Diruhumber et al, 1979] did not reduce brain AChE levels, whereas similar doses of physostigmine inhibited more than 50% of brain AChE activity (FIG. 9B).

In contrast, AChE activity measured in homogenates from the cerebral cortex of drug-injected stressed mice, was reduced by 0.1 mg/kg of either pyridostigmine or physostigmine to less then 50% of normal level (FIG. 9C). The stress treatment therefore reduced the pyridostigmine dose required to inhibit 50% of brain AChE from 1.50 to 0.01 mg/kg. This coincided with a >10-fold increase in brain penetration of either the albumin-binding dye Evans-blue (FIG. 9D) or CMV AChE plasmid DNA [Ben Aziz-Aloya et al 1993] (FIG. 9E) under stress.

As the pyridostigmine doses that inhibited cortical AChE activity in non-stressed mice (>1 mg/kg) were reported to perturb CNS functions in primates [Blick et al, 1994], its effect was examined on mRNA levels of the c-fos oncogene, an indirect marker for enhanced neuronal excitability [Melia et al, 1994], by reverse transcription followed by PCR amplification (RT-PCR). Earlier appearance of PCR product, reflecting over 100-fold increase in brain c-fos mRNA level was evident in stressed as compared with control animals (FIG. 9F), in line with previous reports [Melia et al, 1994]. A similar increase in c-fos mRNA was observed in non-stressed animals as soon as 10 minutes following i.p. injection of 2 mg/kg pyridostigmine (95% inhibition of cortical AChE) (FIG. 10A, upper panel).

To explore the direct effect of pyridostigmine on cholinergic brain circuits, electrophysiological and molecular neurobiology analyses were undertaken on in-vitro maintained brain slices [Friedman and Gutnick, 1989]. Direct application of 1 mM pyridostigmine to hippocampal slices reduced AChE activity within 30 minutes with similar efficacy to that observed in vivo at a dose of 2 mg/kg (data not shown) and induced a parallel 100-fold increase in c-fos mRNA levels. Control tests with primers for synaptophysin mRNA revealed no change either in vivo or in brain slices, demonstrating the selectivity of the above responses (data not shown).

Moreover, the earlier appearance of AChE mRNA product under pyridostigmine administration (FIG. 10A, lower panel), reflects an association between c-fos levels and the transcriptional control of key cholinergic proteins. Electrophysiological recordings in such slices revealed a pyridostigmine-induced increase in the amplitude and rate of rise of evoked population spikes in the CA1 area of the hippocampus, in response to stimulation of the Schaffer Collaterals (FIG. 10B). This enhancement in summated neuronal activity demonstrated directly the increased excitability of the local circuit following pyridostigmine application.

Double-blind human studies testing pyridostigmine effects on 35 young healthy volunteers ("peace time", [Glickson et al, 1991] and additional data, not reported previously) as compared to those observed in 213 treated soldiers during the Gulf War [extension of Sharabi et al, 1991] resemble the current rodent data in this Example. In both human studies each individual was asked to report on a yes/no questionnaire regarding symptoms related to the drug. During peace time, in agreement with previous reports [Taylor, 1990; Borland et al, 1985] documented symptoms were mainly related to peripheral nervous system (PNS) functions (symptoms included: abdominal pain, diarrhea, frequent urination, increased salivation, rhinorrhea and excess sweating) with an average of 18.8% (range: 5.5–38.9%), while only 8.3% (range: 0–16.6%) of participants reported symptoms related to CNS functions (headaches, insomnia, drowsiness, nervousness, difficulties in focusing attention and impaired calculation capacities) (FIG. 11 dashed bars).

Figure 11:
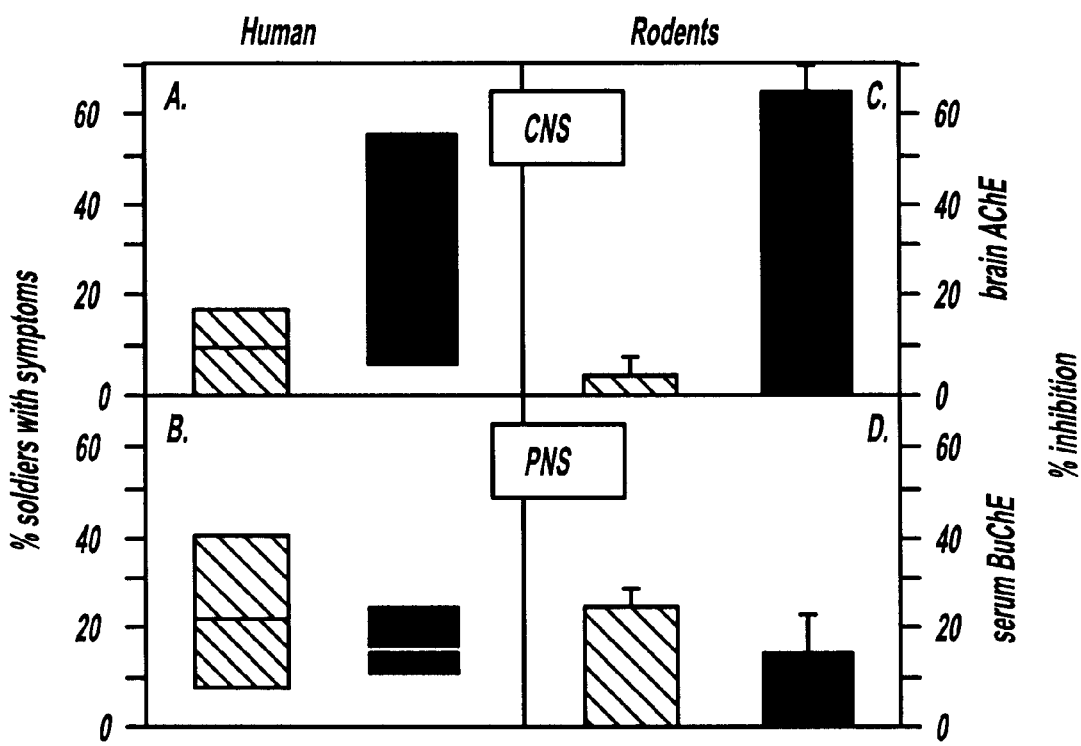
FIGS. 11A–D are graphs showing pyridostigmine effects in humans during peace and war and in non-stressed and stressed rodents. Left panels (A–B): Results of a double blind, placebo controlled study (dashed bars, "peace"). Pyridostigmine (n=18) or placebo (n=17) were administered to healthy young male volunteers. Symptoms were reported at the end of the study. Presented are ranges (%) of soldiers reporting pyridostigmine-induced symptoms related to CNS (A) or PNS (B). During the Gulf War 213 male soldiers aged 18–22 years were questioned, 24 hours after initiation of pyridostigmine treatment (filled bars). Right panels (rodents, C–D): summary of measured brain AChE inhibition (C) and serum BuChE inhibition in mice (D) 10 minutes following injection of 0.1 mg/kg pyridostigmine in non-stressed (control, n=4), and stressed (n=5) mice. Percent inhibition (standard deviation was calculated in comparison to the average activity calculated in non-injected, not-stressed (n=12) and stressed (n=6) animals.
Figure 12:
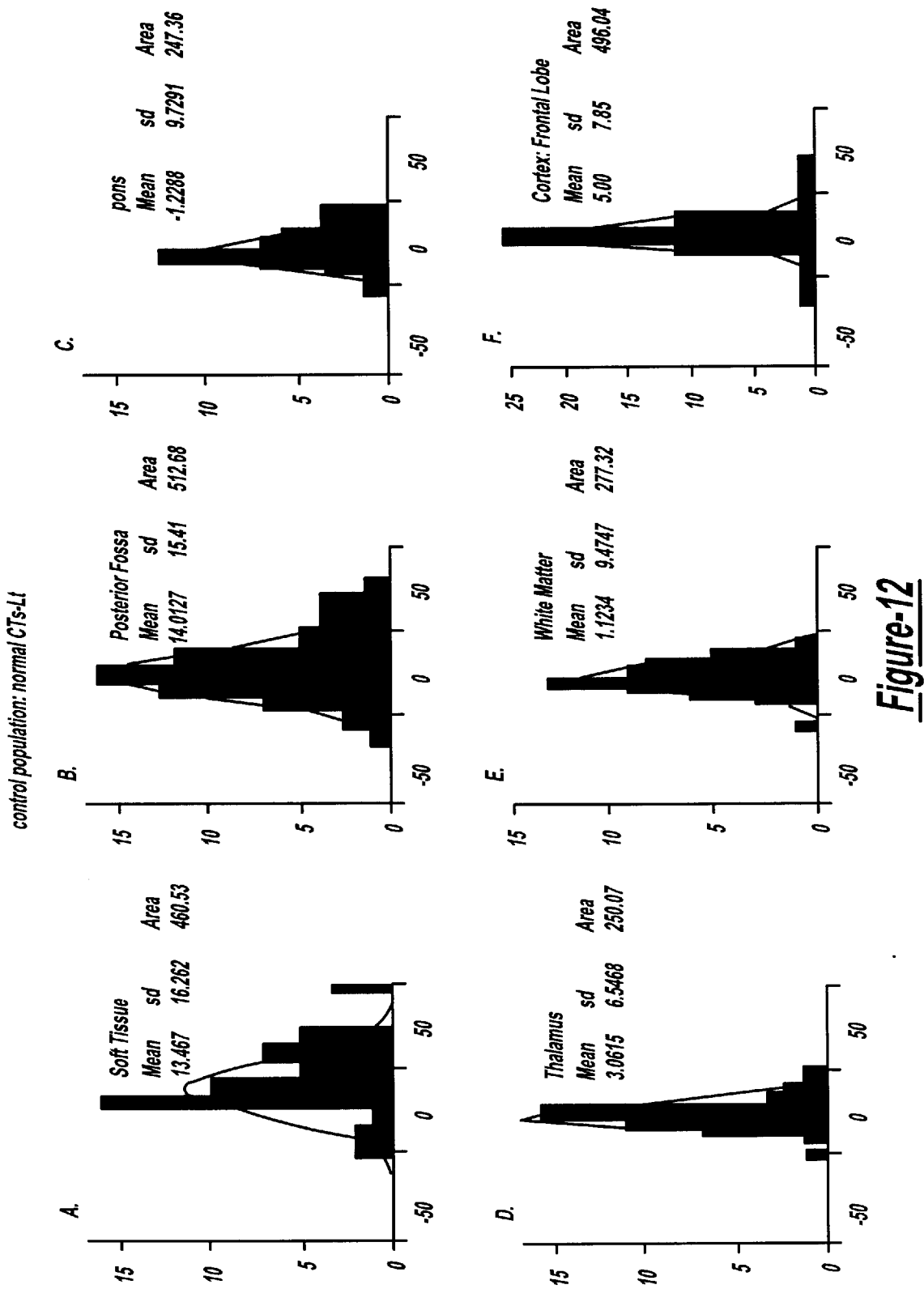
FIGS. 12A–F are graphs showing the CT signal for control population wherein (A) is neck soft tissue, (B) posterior fossa, (C) pons, (D) thalamus, (E) white matter and (F) cortex frontal lobe.

In contrast, extension of the reported study performed during the Gulf War [Sharabi et al, 1991], revealed that 23.6% (range: 6.2–53.4%) of the 213 soldiers reported on CNS symptoms while only 11.4% (range: 6.1–20.4%) reported PNS symptoms (FIG. 11, filled bars). In parallel, in control mice injected with 0.1 mg/kg pyridostigmine, serum BuChE activity was inhibited similarly to that measured in humans at peace time (18.8(3.5% in humans and 20.4(5.5% in mice). Under these conditions, no inhibition of mouse brain AChE was measured (see also FIG. 9B). Injection of similar doses of pyridostigmine to stressed mice caused a significant inhibition of mouse brain AChE, with a tendency toward limitation of BuChE inhibition (FIG. 11). Thus, PNS effects were relatively suppressed and CNS effects-enhanced, probably due to either the restraint stress in mice or the psychological stress associated with war in humans.

These findings demonstrate significant correlation between stress and pyridostigmine-induced CNS effects. These data confirm previously accepted idea that treating non-stressed mice with prophylactic doses of pyridostigmine does not inhibit CNS AChE, corresponding to unaffected CNS functions in non-stressed primates [Blick et al, 1994] or humans at peace time [Borland et al, 1985]. Yet, similar treatment under stress conditions (in mice) was associated with increased brain penetration, significant inhibition of brain AChE activity, increased neuronal excitability and oncogene activation. This increase in c-fos mRNA levels may explain the induction of AChE transcription by the presence of a c-fos binding site in the mammalian AChE promoter [Ben Aziz-Aloya et al, 1993; Ekstrom et al, 1993].

Since central cholinergic neurotransmission systems are normally involved in stress responses [McEwan and Sapolsky, 1995] access of pyridostigmine to the brain can be expected to add yet more "stress like" symptoms to those associated with the war situation. That some of the associated stress effects seen in this Example parallel those reported during the Gulf War further strengthens these observations.

EXAMPLE 2

As shown in Example 1, stress increased permeability of the blood-brain barrier (BBB). This work suggested a link between alteration in BBB permeability and activation of central adrenergic pathways. To test this the BBB permeability to Evans Blue dye was tested in FVB/N mice following stress (forced swim) or administration of adrenaline or atropine.

Control FVB/N mice were injected with 0.1 ml 4% Evans Blue dye (Catalog #E2129, Sigma Chemical Co., St. Louis, Mo.). Mice were also injected similarly 10 minutes after stress-inducing forced swimming [Melia et al, 1994] or an ip injection of adrenaline or atropine (30 mg/kg). After 10 minutes, the mice were sacrificed and brain removed. 200 $\mu$m sections were prepared from fresh tissue, mounted on slides, and examined. Animals were anesthetized with Nembutal during the injection procedures.

Figure 8:
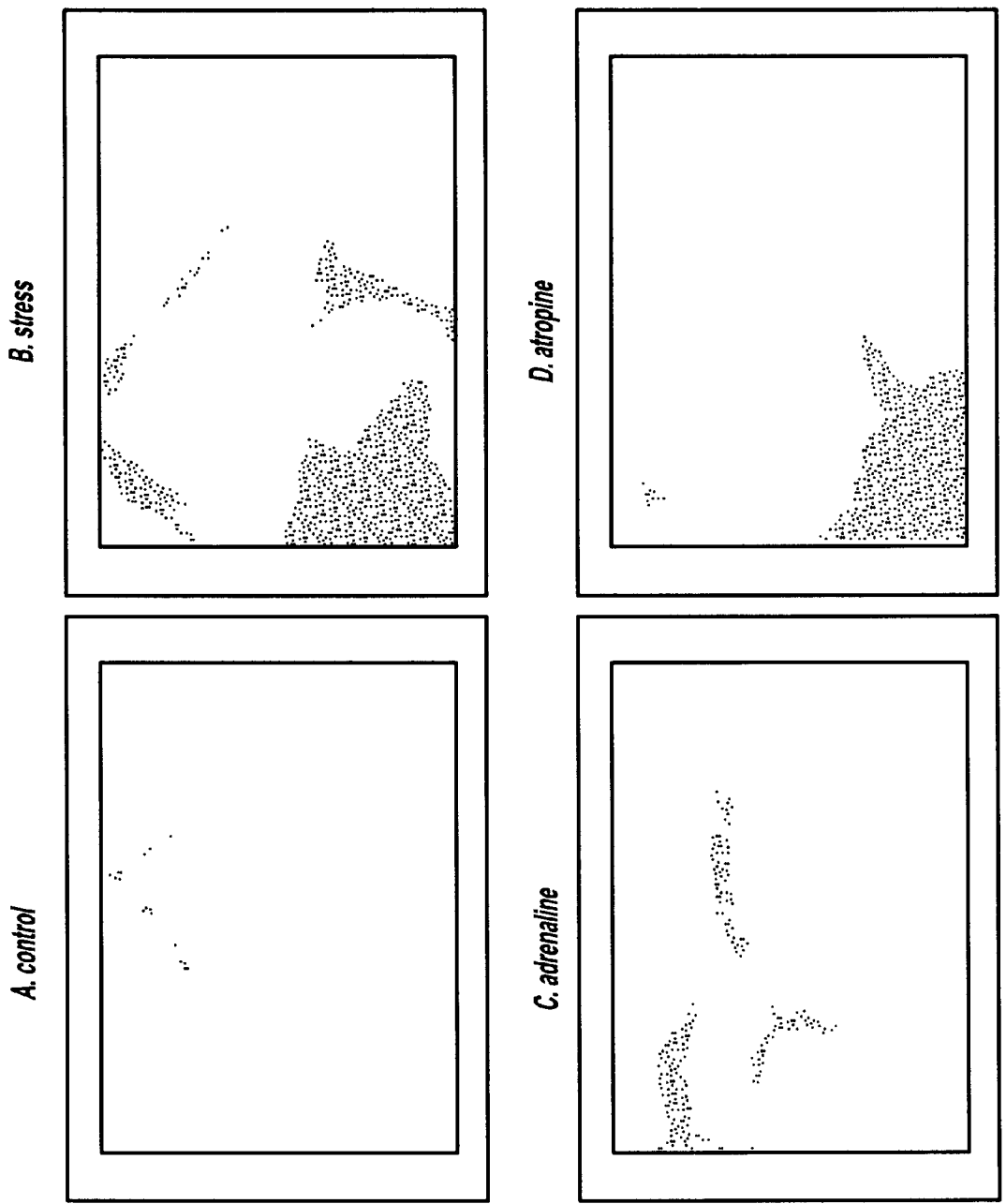
FIGS. 8A–D are photographs of mice brains following injection of Evans Blue Dye and (A) control no other treatment, (B) stress induced by forced swimming, (C) adrenaline and (D) atropine.

Examination of the tissue demonstrated enhanced BBB permeability to Evans Blue following stress and administration of either adrenaline or atropine (FIG. 8). In all mice examined, dye was observed within brain capillaries. However, only in the stress-treated or drug-treated animals could dye be observed to diffusely stain brain tissues. At the administered doses and time course examined, atropine appeared at least as effective as stress in opening the BBB while adrenaline was somewhat less effective.

EXAMPLE 3

Acute traumatic stress may lead to post-traumatic stress disorder (PTSD), a clinical syndrome characterized by delayed neuropsychiatric symptoms such as depression, irritability, restlessness, and impaired cognitive performance [Sapolsky, 1996; Bremmer et al, 1995; Gurvitis et al, 1993]. While it is generally assumed that PTSD is associated with sustained modifications in central cholinergic functions, it is not yet known how a single stressful event might mediate long-term neuronal plasticity. In mammals, acute stress elicits a rapid, transient increase in released acetylcholine (ACh) with a corresponding phase of increased neuronal excitability [Imperato et al, 1991]. Pharmacological blockade of the ACh-hydrolyzing enzyme acetylcholinesterase (AChE) promotes a similar enhancement in electrical activity in cortical neurons [Ennis and Shipley, 1992], presumably by increasing available neurotransmitter. The cholinergic activation associated with both traumatic stress and cholinesterase inhibition, together with the observation that even a single exposure to AChE inhibitors may induce psychopathologies strikingly reminiscent of PTSD [Rosenstock et al, 1991], suggests that the long-term effects of stress and anticholinesterase intoxication may derive from a common pathway initiated by a burst of intense cholinergic activity.

To explore the mechanism(s) by which acute cholinergic stimulation might promote long-term changes in cholinergic neurotransmission, in this Example transcriptional and post-transcriptional regulation of genes encoding key cholinergic proteins following either acute stress (forced swimming) or exposure to anti-cholinesterase drugs and correlated them with electrophysiological activity in the hippocampus were studied.

RT-PCR analysis: Total RNA was extracted from cortex of FVB/N mice sacrificed 80 minutes following 2×4 minutes of forced swimming (stress) or from cortico-hippocampal slices treated with 1 uM DFP (diisopropylfluorophosphate an anti-AChE) for 30 minutes. Care of animals and the conduction of these experiments were in accordance with institutional guidelines. Kinetic follow-up of RT-PCR was performed, using the 375+/1160-primer pair which amplifies the region common to all AChEmRNA subtypes and primer pairs specific for ChAT, c-fos, and synaptophysin mRNAs [Friedman et al 1996; Layer et al, 1995; Beeri et al, 1995]. PCR products were sampled every third cycle, electrophoresed and stained with ethidium bromide. Products from 6 consecutive samples are presented for each experimental group and primer pair in FIG. 3. The first PCR cycle when a product can be detected reflects the initial amount of the corresponding mRNA in the tested sample. A difference of three in the first cycle of appearance of product reflects approximate 8-fold difference in the initial concentration of each specific RNA [Friedman et al, 1989]. Control: RNA from non-treated animals, which revealed similar patterns to non-treated slices (not shown). C-fos RT-PCR traces represent mRNA preparations from 10 minute post-treatment; ACHE, synaptophysin and ChAT products represent RNA preparations from 30 minute following either stress or AChE inhibition.

Stratum oriens fibers were stimulated in hippocampal slices maintained in vitro with a bipolar tungsten electrode as shown in FIG. 3B and the extracellular evoked potentials recorded using glass microelectrodes in the CA1 area before (Control) or 30 minutes following addition of 1(M DFP (Anti-AChE), to the perfusing solution.

Changes in population spikes are shown to be cholinergic (FIG. 4A): One hour administration of 1 or 10 uM carbachol (CCh) increased the amplitude of population spikes (mv) as dependent on excitation intensity [I(mA)] in a dose-dependent manner, suggesting involvement of ACh in this response. Delayed repression of increased population spikes is shown in FIG. 4B and are average and standard deviation values for 6 measurements per point of population spikes evoked in response to the noted stimulus intensities in hippocampal slices under control conditions (control, empty circles), or following 1 or 3 hours under continuous perfusion of 10(M physostigmine (filled circles or squares, respectively). Increased population spikes and their suppression are both mediated by muscarinic synapses as shown in FIGS. 4C1 and C2. Drawn are population spike traces from slices under 1 hour control conditions (cont.), following 1 hour under co-exposure to 1 uM physostigmine and 1 uM atropine (phy+at), or 1 hour after that, when atropine was washed off and under continued exposure to physostigmine. Note the absence of excitation response under atropine and that no suppression took place 1 hour after its removal.

In FIG. 4D Paired-pulse facilitation enhancement is shown to be transient: Drawn are first and second responses (V1, V2) separated by a 500 msec interval or the difference between such responses (V2–V1) following 50, 100 or 500 msec intervals for hippocampal slices under control conditions or following 1 or 3 hours of perfusion with 1 mM physostigmine. Note the prolonged duration and the intense signals of facilitation responses recorded 1 hour following physostigmine addition to the perfusion medium and the suppression of both these responses after 3 hours of such exposure.

Sagittal brain slices were maintained under the above detailed conditions, except that KC1 concentration was modified to 10 mM. RNA extraction followed by RT-PCR amplification demonstrated stable maintenance of mRNA levels for the key genes detailed in this report for as long as 12 hours.

Physiological and transcriptional responses measuring intracellular Ca++ mobilization and Na+ influx were performed (FIG. 5). Prevention of facilitation enhancement was measured by duration of paired-pulse facilitation responses in hippocampal slices under control conditions (empty triangles), 1 hour following the addition of 1 uM pyridostigmine to the perfusion medium (full squares) or 1 hour following treatment with both 1 uM physostigmine and 1 uM BAPTA-AM (full triangles). Note the complete prevention of the physostigmine-induced prolongation of paired-pulse facilitation under BAPTA-AM. Suppression of the transcriptional response was shown with c-fos, ChAT and synaptophysin. mRNAs were PCR-amplified from control slices (cont.) or slices treated for 1 hour with 1 mM pyridostigmine (Pyr) alone, or with pyridostigmine and 1 uM of the Ca++ chelator BAPTA-AM or the Na+ channel blocker tetrodotoxin (TTX). The anti-cholinesterase-induced changes in c-fos and ChAT mRNA were both suppressed by either BAPTA-AM or TTX, demonstrating that these transcriptional changes depend both on the increased intracellular Ca2+ and on Na+ influx.

Figure 6:
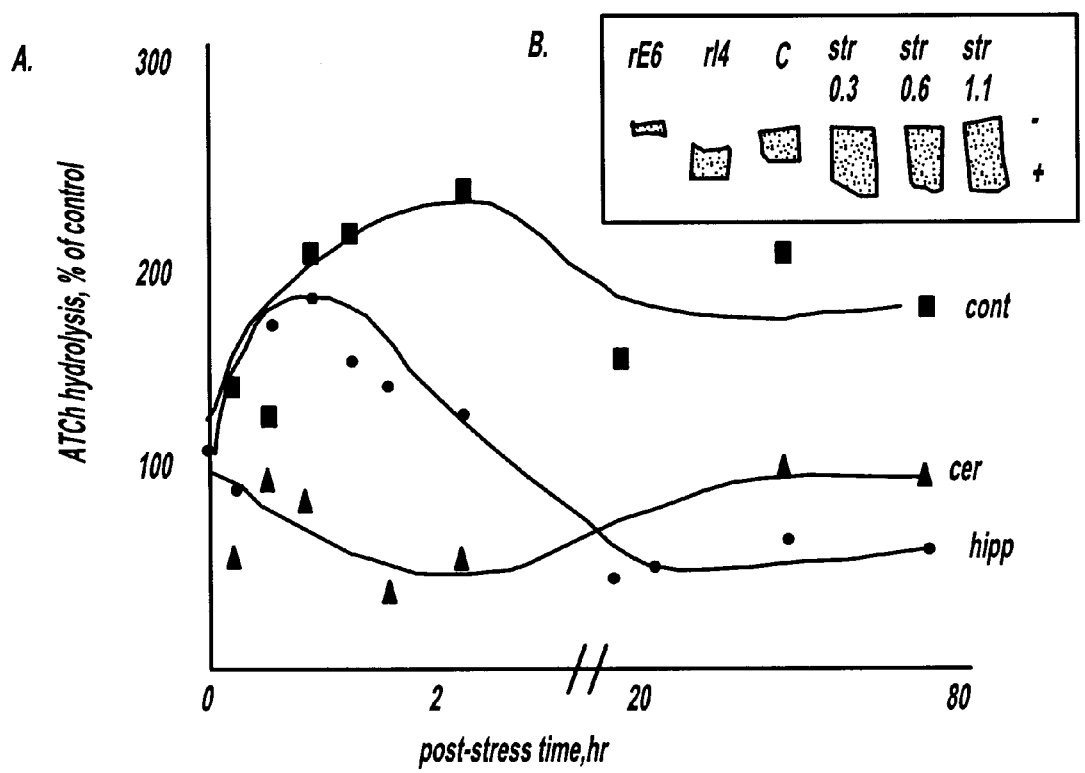
FIGS. 6A–B show long term changes in AChE activity following stress.

Long term changes in AChE activity following stress were measured. Specific AChE activities in (mole acetylthiocholine (ATCh) hydrolyzed per hour per mg tissue were spectrophotometrically determined [Ben Aziz-Aloya et al, 1993) in extracts of cortex, cerebellum or hippocampus prepared from animals sacrificed at the noted times after forced swimming protocol [Melia et al, 1994]. Percent of control activities for each brain region for 10 out of 20 studied mice are shown (FIG. 6) and show stress intensifies cortical AChE activity and diversifies its electrophoretic heterogeneity. Cortical protein extracts were electrophoresed (20 ul per lane, 1:10 w/vol) in 7% non-denaturing polyacrylamide gels. Gels were histochemically stained for catalytically active AChE. Recombinant human E6-AChE (rE6) and I4 AChE (rI4) produced in Xenopus oocytes [Ghosh et al, 1994] (1:5 oocyte/lane) served as known correlates. The post-stress activity and the electrophoretic heterogeneity of cortical AChE increased following stress.

Selective induction of readthrough AChEmRNA following stress and AChE inhibition were measured using kinetic follow-up of RT-PCR. The positions of primer pairs specific for the alternatively spliced AChEmRNA subtypes are presented on the left of the FIG. 7. [Primer pair 1361+/1869– ("E6") detects mRNA encoding the synaptic AChE form; 1361+/175– ("I4/E5") detects both a 549 bp product of readthrough AChEmRNA and a 432 bp product encoding the GPI-lined red blood cell (RBC) form of the enzyme]. Both in vivo stress (forced swimming) and in vitro AChE inhibition promoted significant increases of the readthrough (I4) but not the synaptic (E6) or erythrocyte (E5) forms of AChEmRNA. The bands displayed in the top right hand panel of FIG. 7 represent endpoint PCR products from a reaction using a nested readthrough AChEmRNA primer pair (1361+/74–) detected by hybridization with a radiolabelled probe [Lewis et al, 1967]. In situ hybridization was undertaken using 5 uM thick paraffin-embedded cortical slices were incubated with 50-mer 5'-biotinylated, chemically protected complementary RNA probe [Melia et al 1994] directed against exon 6 initiated at nt.1869 or intron I4 initiated at position 74, of the mouse AChE gene (accession no. x56518). Signals were detected using alkaline phosphatase-streptavidin conjugates and Fast Red as a substrate. FIG. 7B shows cortical layers II–V (upper panels), and magnified pyramidal neurons of cortical layer no. 2 (lower panels). I4 labeling was essentially limited to layers II+V under control conditions, but was intensified and included layer III+IV after exposure to AChE inhibitor (pyridostigmine, 2 mg/kg). Also, the subcellular localization of I4-AChEmRNA shifted from around the nucleus under control conditions to the entire cell bodies and their apical dendrites following AChE inhibition. Stress treatment induced similar changes (not shown).

DISCUSSION

As in Example 1, adult FVB/N mice subjected to either a forced swimming stress-inducing protocol [Melia, et al, 1994] or injected with an AChE inhibitor display dramatic increases in brain mRNAs encoding the early immediate transcription factor c-fos. In vitro, cortico-hippocampal brain slices exposed to various AChE inhibitors displayed enhanced neuronal excitability and similar rapid increases in cortical c-fos gene expression (FIG. 3A). The presence of c-fos binding sites in the promoters of several genes encoding key cholinergic elements, including AChE (Ben Aziz-Aloya et al, 1993], the acetylcholine synthesizing enzyme choline acetyltransferase (ChAT) [Bausero et al, 1993] and the vesicular acetylcholine transporter (VAChT) [Eiden and Erickson, 1997] suggested that acute stress and/or anti-cholinesterase exposure, via cholinergic stimulation and elevated c-fos, might activate regulatory pathway(s) leading to longterm changes in the expression of proteins mediating brain cholinergic neurotransmission.

To examine changes in CNS gene expression associated with acute stress or cholinesterase inhibition, a semi-quantitative RT-PCR [Karpel et al, 1994] was performed on cortical RNA extracted from mice sacrificed 80 minutes following forced swimming or cortico-hippocampal slices [Friedman and Gutnick, 1989] harvested following 30 minute exposure to DFP. These analyses revealed pronounced but opposing changes in the levels of mRNA encoding AChE and those encoding ChAT or VAChT following both stress and DFP.

While AChE mRNA levels were markedly increased as compared with controls, the levels of ChAT and VAChT mRNAs were prominently reduced (FIG. 3A) under both experimental conditions. These changes in gene expression lagged behind elevated c-fos levels by up to 20 minutes (FIG. 3A), consistent with the idea that c-fos plays a role in modulating cholinergic gene expression and that c-fos may either enhance or suppress gene transcription, depending on its interactions with additional factors. Changes in the levels of mRNA encoding synaptophysin, L-type Ca++ channel or glyceraldehyde-phosphodehydrogenase were not observed.

These data therefore implied that acute cholinergic stimulation promotes selective bi-directional changes in gene regulation that act to reduce the bioavailability of acetylcholine through suppressed synthesis/packaging and enhanced hydrolysis of neurotransmitter. Thus, they predicted a delayed phase of reduced neuronal excitability following both stress and AchE inhibition.

To test the hypothesis that acetylcholinesterase inhibitors mediate both acute and delayed phases of cholinergic activity in the brain, electrophysiological recordings were performed in sagittal hippocampal brain slices. Following one hour exposure to DFP, and under a wide range of stimuli intensities, recordings in the CA1 region of the hippocampus revealed increased amplitude, rate of rise and paired-pulse facilitation duration in response to orthodromic stimulation of the CA2/CA3 region of stratum oriens, which contains cholinergic fibers (FIG. 3B). The non-hydrolyzable ACh-analog carbamylcholine induced parallel, dose-dependent increases in signal (FIG. 4A), suggesting a common pathway for the acute hyperactivity elicited by direct receptor activation and that promoted by cholinesterase inhibition. However, when AchE inhibition was extended to 3 hours by continuous perfusion with physostigmine, the enhanced responsiveness of cholinergic pathways to stimulation was prominently muted, approaching that displayed by control slices. This observation allowed the identification of a transient, early phase of excitability and a delayed phase of suppression. Notably, both phases of physostigmine-mediated hyperactivity could be blocked by adding the selective muscarinic antagonist atropine to the perfusion solution during the early phase. This experiment indicated that the late phase of depressed activity depended on a prior, early phase of acute stimulation, and that activation of muscarinic receptor receptors plays and indispensable role in initiating this chain of events. Paired-pulse facilitation examined under the same experimental conditions demonstrated a complementary pattern of hyperexcitability followed by suppressed activity (FIG. 4D). Thus, these data show that a rapid, transient phase of cholinergic activation stimulates a delayed feedback pathway that works to restore basal brain activity and that this regulatory mechanism is controlled by modulated synthesis of the proteins mediating cholinergic neurotransmission.

Since the c-fos gene contains a Ca++-responsive element [Ghosh et al, 1994], it appears that intracellular accumulation of calcium should play a role in translating the transient phase of cholinergic hyperactivation into changes in gene regulation. Indeed, the calcium chelator BAPTA-AM prevented enhanced paired-pulse facilitation (FIG. 5A) and both BAPTA-AM and the sodium channel blocker tetrodotoxin (TTX) attenuated the changes in c-fos and ChAT mRNA levels mediated by AChE inhibition (FIG. 5B). These observations demonstrated a direct correlation between neuronal activity, Ca++-mediated second messenger pathways, and modulations in cholinergic gene expression.

Acetylthiocholine hydrolysis in homogenates from microdissected brain regions at various times following stress treatment revealed 2–3 fold increases in AChE activity within So minutes after stress in both cortex and hippocampus, but not cerebellum (FIG. 6A), in line with findings of others [Tsakiris et al, 1993]. Surprisingly, AChE activity in neocortex of animals exposed to a single stress session remained significantly higher than that observed in control mice for over 80 hours (P<0.005, 2-tailed t test). In contrast, hippocampal AChE activity was elevated for only 4 hours, following which period it had stably dropped back close to control values.

Electrophoretic separation under non-denaturing conditions revealed the presence of novel, fast-migrating AChE form(s) in brains of stressed mice (FIG. 6B). This pattern of gel migration corresponded closely to that of the highly hydrophilic, monomeric, secreted form of catalytically active readthrough AChE produced in heterologous expression systems [Seidman et al, 1995]. The minor readthrough AChEmRNA species was detected in brain and in several tumor cell lines [Karpel et al, 1994], but its protein product had never been unequivocally identified in vivo and its physiological significance is yet unclear.

Following either stress or exposure to AChE inhibitors, a pronounced increase was observed by RT-PCR in the level of the mRNA encoding readthrough AChE in which intron I4 is retained in the mature transcript (FIGS. 7A,B). In contrast, neither the transcript containing alternative 3' exon 6 (E6) and encoding the dominant synaptic form of the enzyme, nor that carrying alternative E5 and encoding the hematopoietic form of AchE displayed detectable changes in their patterns of expression (FIG. 7A,B). Stress, via neuronal excitation, thus mediates not only enhanced transcription, but also modified alternative splicing from the ACHE gene, leading exclusively to de novo synthesis of the unique readthrough AchE isoform.

High resolution in situ hybridization on cortical sections revealed striking qualitative and quantitative differences between control and pyridostigmine-treated animals in the expression of readthrough ACHE mRNA. In controls, signals were relatively weak and restricted to somata of neurons in cortical layers 2 and 5. In contrast, both somata and apical dendrites of neurons from all cortical layers were intensely labeled following exposure to pyridostigmine (FIG. 7B). However, an exon 6-specific probe revealed similar levels of labeling intensities for E6-AChE mRNA in somata of neurons in layers 2 and 3 of the parietal cortex of control and pyridostigmine-treated mice (FIG. 7). That otherwise non-AChE expressing cells begin producing large amounts of a secretable, non-synaptic form of AChE following acute cholinergic stimulation suggests non-cholinergic involvement, implicating the non-catalytic activities of the AChE protein [Small et al, 1995; Jones et al, 1995; Layer and Willbold, 1995].

These findings demonstrate that the sequence of events common to the brain's responses to acute stress and to cholinesterase inhibitors initiates with a brief phase of neuronal excitability. This triggers within a few minutes rapid induction of c-fos that mediates hours-long selective regulatory effects on the transcription activities of several genes involved directly or indirectly in acetylcholine metabolism. This rapidly floods the intercellular spaces with acetylcholine-hydrolyzing potential, which can play a crucial role in short-term quieting of brain activity following a traumatic experience.

EXAMPLE 4

Effect of Swim Stress on the Blood Brain Barrier to Horseradish Peroxidase

Forced swim induced stress has been shown to increase brain penetration of Evans Blue (Example 2). However, a detailed evaluation of the anatomical distribution stress induced perturbations in BBB within the brain was not explored. This Example uses horseradish peroxidase (HRP) to study the effects of stress on the BBB and anatomical distribution of the dye due to stress (FIG. 14A). Horseradish peroxidase also has been used to study changes in the BBB, often in parallel to Evan's Blue [Broadwell et al, 1982; Wijsman et al., 1993]. However, unlike Evans Blue, a permanent color product can formed by the histochemical reaction of HRP with diaminobenzidine. Since direct histochemical staining of exogenous HRP may be difficult to distinguish from endogenous peroxidases we have employed an antibody specific to HRP that enables immunohistochemical localization of HRP. This immunohistochemical protocol also provides a permanent color. Methods: Male mice were assigned to two groups: The experimental group (n=3) was exposed to swim stress (2×4 minute swims with 4 minute rest between swims as described herein above) prior to HRP injection and the control group (n=3) remained in the home cage prior to HRP injection. 90 mg HRP was dissolved in saline and then diluted 1:1 with 0.2% solution of Evans Blue (as a tracer). 0.1 ml HRP was injected into the tail vein under pentobarbital anesthesia. Mice were sacrificed 15 minutes after injection of HRP. Brains were fixed by transcardial perfusion of 4% paraformaldehyde in 0.1 M phosphate buffered saline, pH 7.4 at room temperature, which also contained 4% sucrose [Shoham et al, 1997]. Duration of perfusion was 8–10 minutes. A sagittal cut was made to separate the two hemispheres, and the tissue cut into coronal blocks and immersed in the same fixative as in the perfusion but at ice temperature. After 24 hours, the tissue was transferred to 10% sucrose in 0.1M PBS. For immunohistochemical staining, 30 µm floating sections were collected in a cryopreservation buffer and kept at −20° C. until processing. The first step of immunohistochemical processing was to quench endogenous peroxidase activity by incubation of brain sections with hydrogen peroxide [Shoham et al, 1997]. Then sections were incubated with Rabbit anti HRP from Jackson ImmunoResearch, USA, at a dilution of 1:100, first at room temperature for 1 hour and then overnight refrigerated. Subsequently sections were processed through a standard biotin-extravidin-peroxidase procedure in which the final color reaction was produced using DAB as a substrate with the addition of nickel ammonium sulfate [Shoham et al, 1997] and specific areas evaluated: CA2 (I), CA3 (II), Piriform cortex (III), hypothalamus (IV) and chorioid plexus (V) as shown on FIG. 14A.

The forced swimming stress increased penetration of HRP into brain (Table 2, FIG. 14B). In both stressed and control mice, staining in blood vessels is expected after intravenous administration and this was confirmed in both stressed and unstressed mice. Staining in choroid plexus and ventromedial hypothalamus is also predictable since these areas are less protected by a BBB. However, even in hypothalamus, in the stressed animal staining spread from the ventricular wall to individual cells of the arcuate nucleus of hypothalamus. Based on their morphology, at least some of these cells were neurons.

With regard to other brain regions, the hippocampus had the highest number of stained cells. These cells appeared to be interneurons. The fact that in the control mouse the only stained cells appeared in the CA3 subregion of hippocampus and very close to the lateral ventricle suggests the spread of HRP first to the cerebrospinal fluid and then into brain regions. In the stressed mouse, stained cells appeared in all subregions of the hippocampus. Furthermore, dendrites of pyramidal cells from CA1 were stained.

Staining of white matter such as the corpus callosum may represent diffusion of HRP from CSF into brain tissue. However, staining of piriform cortex and retrosplenial cortex may involve more than diffusion from CSF since theoretically the entire cortex is surrounded by CSF and should have been stained if diffusion was the only mechanism. The differential staining of piriform and retrosplenial cortex may be related to reactivity of these brain regions in response to some stressful situations. In a different study using these two brain regions displayed increased uptake of radioactive 2-deoxyglucose following swim stress [Duncan et al, 1993]. Thus, within the context of swim-stress, the pattern of the staining observed in this Example matches the pattern of induced metabolic activity.

In other stress-inducing situations, the piriform and retrosplenial cortices have also been exhibit increased expression of c-fos mRNA [Imaki et al, 1993]. However, the pattern of brain regions which react to stress varies with the stress-inducing situation. Thus, for example, if stress is induced by foot-shock or by a stimulus associated with foot-shock, the central nucleus of the amygdala increases its metabolic activity [Campeau et al, 1991]. If stress is induced by immobilization stress, then metabolic activity is increased in the paraventricular nucleus of thalamus and hypothalamus and in the habenula but not in the amygdala [Chastrette et al, 1991]. In contrast, in the swim stress paradigm there is no increase in 2-deoxyglucose uptake or in FOS expression in the central nucleus of the amygdala or in the paraventricular nucleus of the hypothalamus [Duncan et al, 1993]. Thus, the absence of HRP staining in these regions in these stressed mice is consistent with the anatomical pattern of activation unique to swim stress.

Together, these data provide further progress in mapping the disruption of the BBB induced by acute stress, and offers indications for the brain regions most likely to be affected by stress-induced perturbations of BBB integrity. As such, they will serve as a basis to evaluate the development pharmacological strategies for transient opening of the BBB based on the stress paradigm. Moreover, the strong HRP staining of the hippocampus following forced swimming indicates that this area brain region should be used for drug delivery protocols using this approach.

EXAMPLE 5

Computerized Tomography (CT) Reveals Disruption of the BBB IN Patients with Neuropathologies with Associated Cholinergic Changes CT is used to detect brain tumors by visualizing their contours, using an electron-dense probe. CT scans are taken before and after prove injections and intensified signals are sought for by automated measurements of electron density. Neuwelt et al [1980b, 1979] has used CT to monitor chemotherapy delivery in patients with brain tumors and using osmotic disruptions. Therefore for the present invention, this same technology is used to determine if the BBB is disrupted in patients who do not have brain tumors and can be correlated with cholinergic changes as disclosed by the present invention. It can test where the disruption takes place and provides a quantifiable method to establish its intensity in response to the stress-mimicking treatments and agents of the present invention.

It is expected that in a control patient, with no tumor, the CT scan will be normal and there will be no penetrance of the electron dense dye into the CNS. 30 scans of normal patients were taken and no disruption of the BBB was seen (FIG. 12A–F). Average signal values were significantly lower than standard deviations in five brain regions (posterior fossa, pons, thalmus, white matter and frontal left cortex). These findings differed from those in the neck's soft tissue, which is not protected by the BBB, where mean signal values were considerably higher than those in brain regions (13.5 as compared with 4.0, −1.2, 3.1, 1.1 and 5.0, for the above regions respectively) and standard deviation close to signal value.

Figure 13:
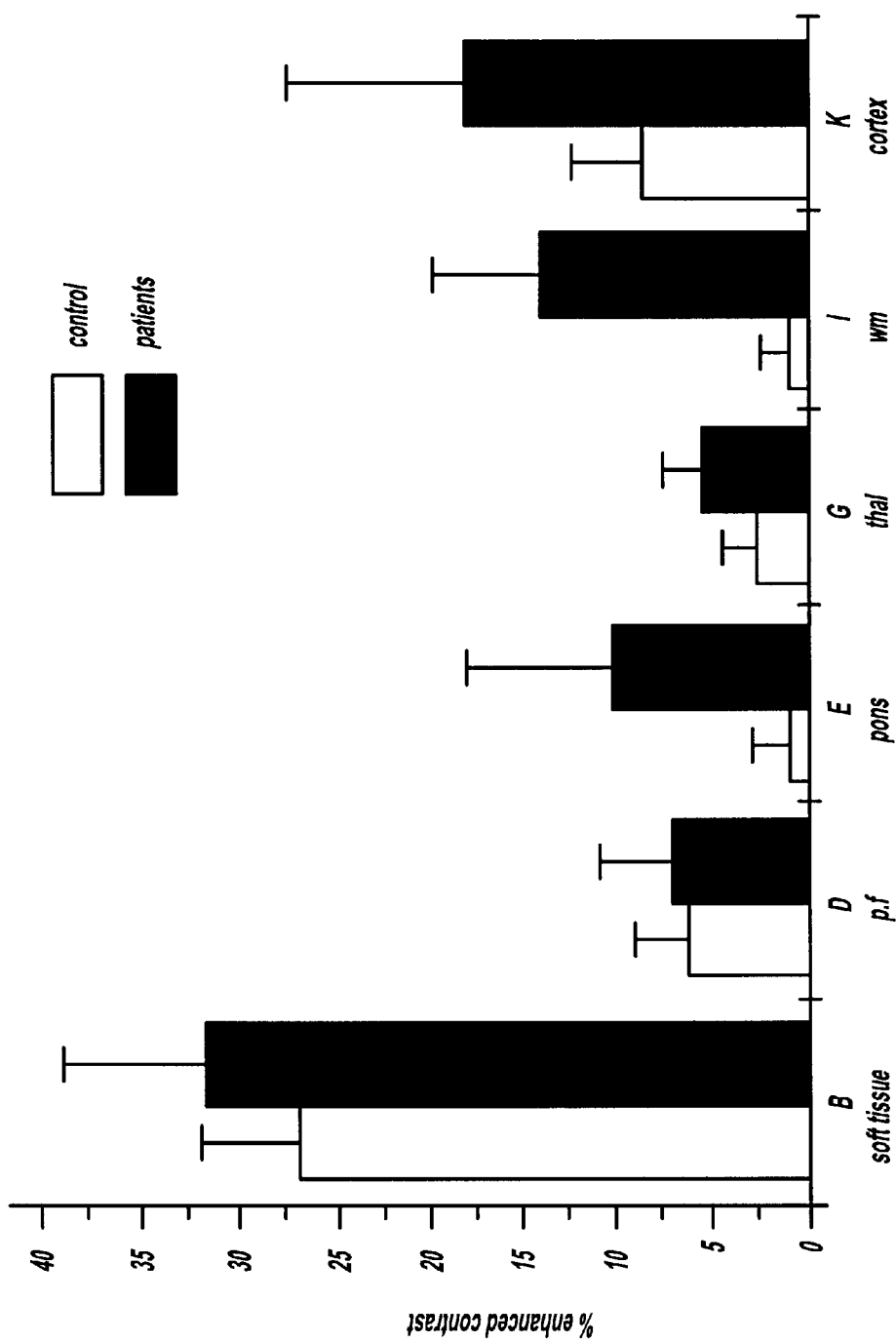
FIG. 13 is a graph of control versus neurological patients showing the percent of enhanced contrast between the two groups wherein p.f. is posterior fossa, thal is thalamus and wm is white matter.

Parallel tests in 30 neurological patients revealed a totally different picture. Signals (percent enhanced contrast as compared with scans taken prior to probe injection) were essentially similar to those of the control group in the neck tissue and in the posterior fossa, considered not to be close to the BBB border. In contrast, signals in pons, white matter and frontal cortex were both increased (by 2–7 fold) and diversified (i.e. displayed large standard deviations) than those in control subjects (FIG. 13).

In the neurologic patients, CSF total protein levels and activities of BChE and AChE were measured as well. A positive correlation was found between probe signal in brain CT to total protein levels measured in the CSF. Patients with normal levels of CSF protein levels had probe signals similar to that found in the controls. Patients with abnormally high protein levels had also abnormally high probe signals, indicating a BBB disruption. It appears likely that the BBB disruption allowed serum protein to enter the CSF. Also there was clear correlation between the BChE and AChE activities, with most patients grouped together and having close values for both enzymes (0–0.5 mOD/min for acetylcholine or butyrylcholine hydrolysis). However, five patients had considerably higher ChE activities in their CSF, either because of excessive synthesis or due to penetrance from the circulation. Moreover, these patients were the patients in which the brain signals had increased the most.

EXAMPLE 6

Pharmacologically-Induced Penetration of the Blood-Brain Barrier

As shown in Examples 2 and 4 herein above, studies of penetration of blood-brain barrier disruption have in the past depended on injection of traceable agents, such as dyes, with the measurement of the agent in the CNS determining how much disruption of the BBB had occurred. However, these agents either are measured in a post-mortem analysis of the brain or using CT scans (Example 5). It would be useful to have a more rapid and sensitive assay in animal models for use in screening BBB integrity.

A rapid physiological assay has been developed based on the reduction in body temperature induced in mice by centrally acting acetylcholinesterase (ACHE) inhibitors. In the assay pyridostigmine is used. Pyridostigmine is generally excluded from the CNS (see Example 1). However, perturbations leading to an opening/disruption in the BBB allow increased access of pyridostigmine to the CNS as shown in Example 1. This increased access of pyridostigmine in the CNS leads to reduction in body temperature which can be monitored. Therefore the assay requires the administration of pyridostigmine together with a compound (or combinations of compounds) to test the efficacy of the compound to disrupt (open) the BBB to allow (facilitate) passage of pyridostigmine across the BBB. The body temperature is then monitored for several hours to determine whether the BBB has opened and the duration. This method also allows for the determination of optimal doses of compounds being tested.

Adult, female FVB/N mice (3 per group) were injected intraperitoneally (ip) with freshly prepared pyridostigmine (0.6 mg/kg body weight) alone or together with the drug or drug combinations to be tested. In this Example dopamine (DA, 1.0 mg/kg) an α adrenergic agonist and propanolol (0.04 mg/kg) a β adrenergic antagonist or the combination of DA and propanolol were tested. Rectal body temperature was monitored for 180 minutes at 20 minute intervals. A single temperature measurement was made 25 minutes prior to the injection to acclimate the animals to the procedure.

Figure 15:
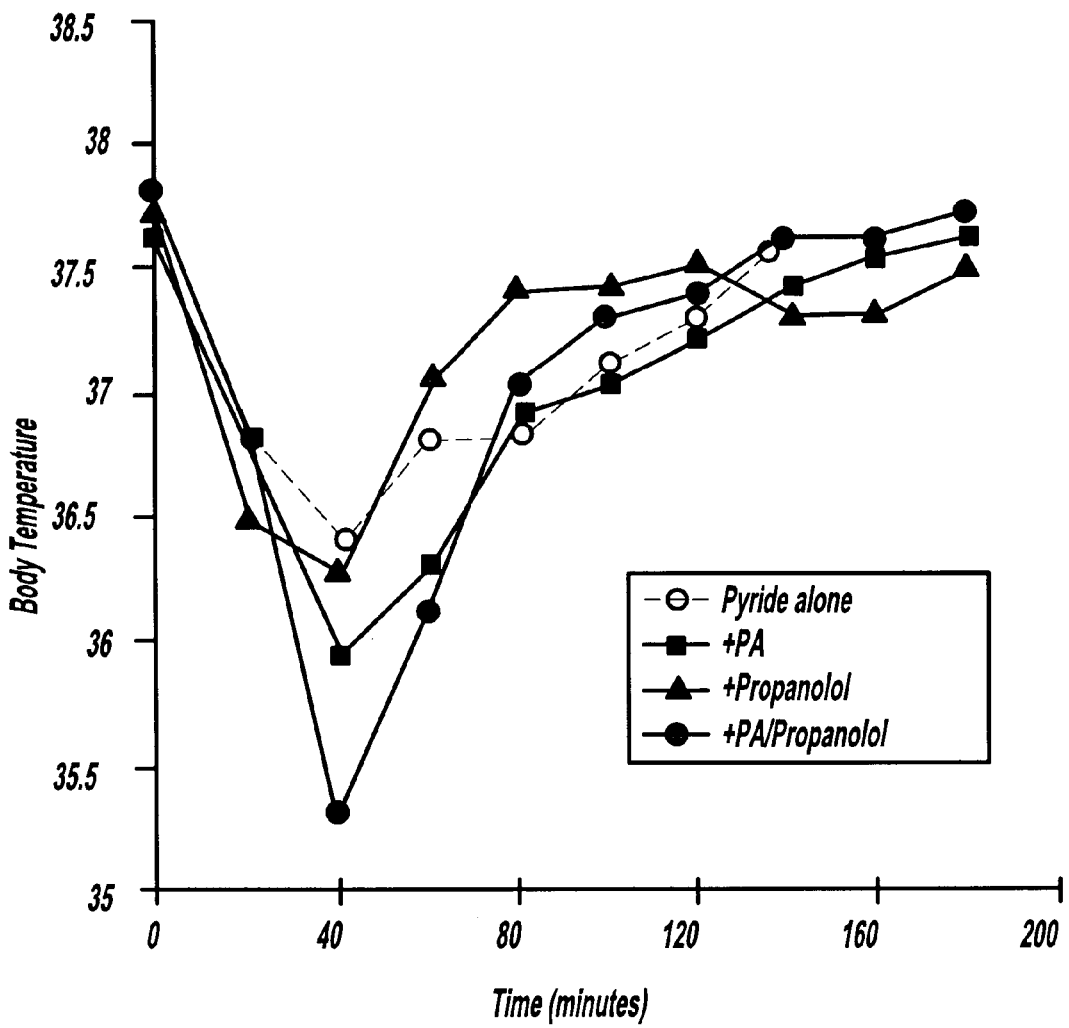
FIG. 15 is a graph showing the response to stress mimicking adrenergic manipulation of the BBB to pyridostigmine wherein —O— is pyridosigmine only, —■— is pyridostigmine plus dopamine (DA), —▲— is pyridostigmine plus propanolol and —●— is pyridostigmine plus DA and propanolol.

As shown in FIG. 15, pyridostigmine alone or together with propanolol induced a 1 to 1.5° C. reduction in body temperature within 40 minutes. Body temperature returned to normal by 80 minutes post injection. Coinjection with DA enhanced the reduction by approximately 0.5° C. However, coadministration of DA and propanolol effected a synergistic effect on pyridostigmine permeability of the BBB. The combination induced reduction in body temperature of approximately 2.5° C. in the same time window.

The simultaneous activation of α adrenergic receptors together with blocking of β adrenergic receptors effects a synergistic effect on BBB permeability.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Readthrough AChB-I4, the I4 sequence is underlined.

Met Arg Pro Pro Gln Cys Leu Leu His Thr Pro Ser

Leu Ala Ser Pro Leu Leu Leu Leu Leu Trp Leu

Leu Gly Gly Gly Val Gly Ala Glu Gly Arg Glu Asp

Ala Glu Leu Leu Val Thr Val Arg Gly Gly Arg Leu

Arg Gly Ile Arg Leu Lys Thr Pro Gly Gly Pro Val

Ser Ala Phe Leu Gly Ile Pro Phe Ala Glu Pro Pro

Met Gly Pro Arg Arg Phe Leu Pro Pro Glu Pro Lys

Gln Pro Trp Ser Gly Val Val Asp Ala Thr Thr Phe

Gln Ser Val Cys Tyr Gln Tyr Val Asp Thr Leu Tyr

Pro Gly Phe Glu Gly Thr Glu Met Trp Asn Pro Asn

Arg Glu Leu Ser Glu Asp Cys Leu Tyr Leu Asn Val

Trp Thr Pro Tyr Pro Arg Pro Thr Ser Pro Thr Pro

Val Leu Val Trp Ile Tyr Gly Gly Gly Phe Tyr Ser

TABLE 1-continued

```
Gly Ala Ser Ser Leu Asp Val Tyr Asp Gly Arg Phe

Leu Val Gln Ala Glu Arg Thr Val Leu Val Ser Met

Asn Tyr Arg Val Gly Ala Phe Gly Phe Leu Ala Leu

Pro Gly Ser Arg Glu Ala Pro Gly Asn Val Gly Leu

Leu Asp Gln Arg Leu Ala Leu Gln Trp Val Gln Glu

Asn Val Ala Ala Phe Gly Gly Asp Pro Thr Ser Val

Thr Leu Phe Gly Glu Ser Ala Gly Ala Ala Ser Val

Gly Met His Leu Leu Ser Pro Pro Ser Arg Gly Leu

Phe His Arg Ala Val Leu Gln Ser Gly Ala Pro Asn

Gly Pro Trp Ala Thr Val Gly Met Gly Glu Ala Arg

Arg Arg Ala Thr Gln Leu Ala His Leu Val Gly Cys

Pro Pro Gly Gly Thr Gly Gly Asn Asp Thr Glu Leu

Val Ala Cys Leu Arg Thr Arg Pro Ala Gln Val Leu

Val Asn His Glu Trp His Val Leu Pro Gln Glu Ser

Val Phe Arg Phe Ser Phe Val Pro Val Val Asp Gly

Asp Phe Leu Ser Asp Thr Pro Glu Ala Leu Ile Asn

Ala Gly Asp Phe His Gly Leu Gln Val Leu Val Gly

Val Val Lys Asp Glu Gly Ser Tyr Phe Leu Val Tyr

Gly Ala Pro Gly Phe Ser Lys Asp Asn Glu Ser Leu

Ile Ser Arg Ala Glu Phe Leu Ala Gly Val Arg Val

Gly Val Pro Gln Val Ser Asp Leu Ala Ala Glu Ala

Val Val Leu His Tyr Thr Asp Trp Leu His Pro Glu

Asp Pro Ala Arg Leu Arg Glu Ala Leu Ser Asp Val

Val Gly Asp His Asn Val Val Cys Pro Val Ala Gln

Leu Ala Gly Arg Leu Ala Ala Gln Gly Ala Arg Val

Tyr Ala Tyr Val Phe Glu His Arg Ala Ser Thr Leu

Ser Trp Pro Leu Trp Met Gly Val Pro His Gly Tyr

Glu Ile Glu Phe Ile Phe Gly Ile Pro Leu Asp Pro

Ser Arg Asn Tyr Thr Ala Glu Glu Lys Ile Phe Ala

Gln Arg Leu Met Arg Tyr Trp Ala Asn Phe Ala Arg

Thr Gly Asp Pro Asn Glu Pro Arg Asp Pro Lys Ala

Pro Gln Trp Pro Pro Tyr Thr Ala Gly Ala Gln Gln

Tyr Val Ser Leu Asp Leu Arg Pro Leu Glu Val Arg

Arg Gly Leu Arg Ala Gln Ala Cys Ala Phe Trp Asn

Arg Phe Leu Pro Lys Leu Leu Ser Ala Thr Gly Met

Gln Gly Pro Ala Gly Ser Gly Trp Glu Glu Gly Ser

Gly Ser Pro Pro Gly Val Thr Pro Leu Phe Ser Pro
```

TABLE 2

The following Table summarizes the histochemical data distribution of HRP- immunohistochemical staining for the animals from which the sections depicted in FIG. 14 were taken

| Brain region | non-stressed control | stressed |
|---|---|---|
| Choroid plexus | + | + |
| HRP in blood vessels | + | + |
| Medial hypothalamus (arcuate nucleus) | + (diffuse staining) | + (diffuse staining plus staining of cells) |
| Piriform cortex | diffuse staining restricted to the tip of the cortex | diffuse staining but covering a greater area than in C3 |
| Retrosplenial cortex | diffuse staining at the upper tip. | diffuse staining but covering a greater area than in C3 |
| Hippocampus, CA3 | diffuse staining plus staining of cells | diffuse staining plus staining of cells (more than in C3) |
| Hippocampus, CA1-2 | no staining | staining of cells |
| Corpus callosum | little staining | extensive staining of fibers |

REFERENCES

Andres et al. (1997). ACHE transgenic mice display embryonic modulations in spinal cord CHAT and neurexin gene expression followed by late-onset neuromotor deterioration. Proc. Natl. Acad. Sci. USA 94, 8173.

Bausero, et al (1993) Identification and analysis of the human choline acetyltransferase gene promoter. Neuroreport 4:287.

Ben Aziz-Aloya et al (1993) Expression of a human acetylcholinesterase promoter-reporter construct in developing neuromuscular junctions of Xenopus embryos. Proc. Natl. Acad. Sci. U.S.A., 90, 2471–2475.

Ben-Nathan, et al, 1991. Stress-induced neuroinvasiveness of a neurovirulent noninvasive Sindbis virus in cold or isolation subjected mice. Life Sci. 48:1493–1500.

Betz et al, 1994. Blood-Brain-Cerebrospinal Fluid Barriers. Chapter 32 in Basic Neurochemistry (5th Edition, Eds Siegel, Albers, Agranoff, Molinoff), pp 681–701.

Bickel, et al., 1993. Pharmacologic effects in vivo in brain by vector-mediated peptide drug delivery. Proc. Natl. Acad. Sci. USA 90(7)2618–2622

Blick, et al. Acute behavioral toxicity of pyridostigmine or soman in primates. Toxicol. Appl. Pharmacol. 126, 311–318 (1994).

Borland, et al., Studies on the possible central and peripheral effects in man of a cholinesterase inhibitor (pyrilostigmine). Hum. Toxicol. 4, 293–300 (1985).

Breaking the Brain Barrier in The Economist, Jan. 4, 1997.

Bremner et al (1995) MRI-based measurement of hippocampal volume in patients with combat-related posttraumatic stress disorder. Am. J. Psychiatry 152:973

Brem et al., 1993. Polymers as controlled drug delivery devised for the treatment of malignant brain tumors. Eur. J. Pharm. Biopharm 39:2–7.

Broadwell et al. Morphologic effect of dimethyl sulfoxide on the blood-brain barrier. Science 217:164–166, 1982.

Brust, Blood-brain-barrier transport under different physiological and pathophysiological circumstances including ischemia. Exp.Pathol. 42, 213–219 (1991).

Campeau et al. Induction of c-fos proto-oncogene in rat amygdala during unconditioned and conditioned fear. Brain Res. 565:349–352, 1991.

Chastrette et al. Effects of daytime and night-time stress on Fos-like immunoreactivity in the paraventricular nucleus of the hypothalamus, the habenula, and the posterior paraventricular nucleus of the thalamus. *Brain Res.* 563:339–344, 1991.

Deyi, et al., The inhibition and protection of cholinesterase by physostigmine and pyridostigmine against soman poisoning in vivo. Fundam. Appl. Toxicol. 1, 217–221 (1981).

Diruhumber, et al., The protection of primates against soman poisoning by pretreatment with pyridostigmine. J. Pharmacol. 31, 295–299 (1979).

Duncan et al. Topographic patterns of brain activity in response to swim stress: Assessment by 2-deoxyglucose uptake and expression of Fos-like immunoreactivity. *J. of Neurosci.* 13:3932–3943, 1993.

Ekstrom, et al., Promoter elements and transcriptional regulation of the acetylcholinesterase gene. DNA.Cell.Biol. 12, 63–72 (1993).

Eiden and Erickson, The Vesicular acetylcholine transporter and the VAchT/ChAT gene locus". J. Neurochem, in press.

Ennis and Shipley, 1992. Tonic activation locus coeruleus neurons by systemic or intracoerulear microinjection of an irreversible acetylcholinesterase inhibitor: Increased discharge rate and induction of c-fos. *Exp. Neurol.* 118:164–177.

Friedman et al. (1996). Pyridostigmine brain penetration under stress enhances neuronal excitability and induces early immediate transcriptional response. Nature Medicine 2, 1382–1385.

Friedman and Gutnick, (1989) Intracellular calcium and control of burst generation in neurons of guinea-pig neocortex in vitro. Europ. J. Neurosci. 1:374–381.

Ghosh, et al (1994) Calcium regulation of gene expression in neuronal cells. J. Neurobiol. 25, 294–303.

Glickson, et al. The influence of pyridostigmine on human neuromuscular functions - studies in healthy human subjects. Fund. Appl. Toxicol. 16, 288–298 (1991).

Goldstein and Betz, 1986. The Blood-Brain Barrier. *Scientific American, September,* 1986, pp 74–83.

Gurvits, et al (1993) Neurological status of vietnam veterans with chronic posttraumatic stress disorder. J. Neuropsychiatry Clin. Neurosci. 5:183

Harik and Kalaria, Blood-brain-barrier abnormalities in Alzheimer's disease. Ann. New York Acad. of Sci. 640, 47–52 (1991).

Imaki T et al. Intracerebroventricular administration of corticotropin-releasing factor induces c-fos mRNA expression in brain regions related to stress response: comparison with pattern of c-fos mRNA induction after stress. *Brain Res.* 616:114–125, 1993.

Imperato, et al, 1991. Changes in brain dopamine and acetylcholine release during and following stress are independent of the pituitary-adrenocortical axis. *Brain Res.* 538:111–117.

Jones et al (1995) The effect of acetylcholinesterase on outgrowth of dopaminergic neurons in organotypic slice culture of rat mid brain. Cell Tissue Res. 279: 323–330

Karpel, et al (1994) Expression of three alternative acetylcholinesterase messenger RNAs in human tumor cell lines of different tissue origins. Exptl.Cell Res. 210, 268–277

Karpel, et al (1996) Overexpression of alternative human acetylcholinesterase forms modulates process extensions in cultured glioma cells. J. Neurochem., 66, 114–123.

Lallement, et al, (1991). Effects of soman-induced seizures on different extracellular amino acid levels and on glutamate uptake in rat hippocampus. Brain Res 563(1–2):234–240.

Layer and Willbold, (1995). Novel functions of cholinesterases in development, physiology and disease. Prog. Histochem. Cytochem. 29:1–99.

Lewis et al (1967). Conformation from choline acetylase analyses of a massive cholinergic innervation to the rathippocampus. J. Physiol. Lond. 191, 215–224.

McEwen and Sapolsky, Stress and cognitive function. Curr. Opin. in Neurobiol. 5, 205–216 (1995).

Melia, et al, Induction and habituation of immediate early gene expression in rat brain by acute and repeated restraint stress. J. Neurosci. 14, 5929–5938 (1994).

Neuwelt and Fraenkel, 1980a. Is there a therapeutic role of blood-brain barrier disruption? Annals Int Med 93(1):137–139 (editorial note).

Neuwelt et al, 1980b. The use of enhanced comouterized tomography to evaluate osmotic blood brain barrier disruption. Neurosurgery 6:49–56.

Neuwelt et al, 1979. Osmotic blood-brain barrier disruption: computerized tomographic monitoring of chemotherapeutic agent delivery. J Clin Inves. 64:684–688.

Neville, et al., Anionic site interactions in human butyrylcholinesterase disrupted by two single point mutations. J. Biol. Chem. 265, 20735–20738 (1990).

Pardridge, et al., 1992. Blood-brain barrier and new approaches to brain drug delivery. *West J. Med.* 156(3) 281–286

Pardridge, 1992. Recent Developments in peptide drug delivery to the brain. *Pharm. Toxicol.* 71(1):3–10

Petrali et al, 1991. Effect of an anticholinesterase compound on the ultrastructure and function of the rat blood-brain barrier: a review and experiment. J Submicrosc Cytol Pathol 23(2):331–338.

Putnam, 1992. Using hypnosis for therapeutic abreactions. *Psychiatr. Med.* 10(1):51–65.

Rachinsky, et al., Molecular cloning of mouse acetylcholinesterase: tissue distribution of alternatively spliced mRNA species. Neuron. 5, 317–327 (1990).

Rosenstock et al (1991) Chronic central nervous system effects of acute organophosphate pesticide intoxication. Lancet. 338, 223–227

Sapolsky, (1996) Why stress is bad for your brain. Science 273:749–750

Seidman et al. (1995) Synaptic and epidermal accumulations of human acetylcholinesterase is encoded by alternative 3'-terminal exons. Mol. Cell. Biol. 15, 2993–3002.

Shoham S et al. Nitric oxide synthase in ventral forebrain grafts and in early ventral forebrain development. *Dev. Brain Res.* 99:155–166, 1997.

Small et al (1995) Cholinergic regulation of neurite outgrowth from isolated chick sympathetic neurons in culture. J. Neurosci. 15:144–151

Sharma, et al, 1991. Increased blood-brain barrier permeability following acute short-term swimming exercise in conscious normotensive young rats. *Neurosci. Res.* 10:211–221.

Sharabi, et al. Survey of symptoms following intake of pyridostigmine during the Persian gulf war. Isr. J. Med. Sci. 27, 656–658 (1991).

Solomon, et al, 1992. The efficacy of treatments for post-traumatic stress disorder. An empirical review. *JAMA* 268(5) :633–638.

Spiegel, 1992. The use of hypnosis in the treatment of PTSD. *Psychiatr. Med.* 10(4):21–30.

Taylor, Cholinergic agonists, Anticholinesterase Agents. In: The Pharmacological Basis of Therapeutics. 8th Ed., (Eds: Gilman A. G., Rall T. W., Nies A. S. & Taylor P.), pp. 122–130, 131–147 (1990). Pergamon Press, New York.

Tsakiris and Kontopoulos (1993) Time changes in Na+, K+-ATPase, Mg++-ATPase, and acetylcholinesterase activities in the rat cerebrum and cerebellum caused by stress. Pharmacol. Biochem. Behav. 44:339–42.

Tuomanen, 1993. Breaching the blood-brain barrier. *Scientific American February* 1993, 268:80–84.

Uyama, et al. Quantitative evaluation of vascular permeability in the gerbil brain after transient ischemia using Evans blue fluorescence. J. Cerebral Blood Flow and Metabolism, 8, 282–284 (1988).

Wijsman J A et al. Heat stress affects blood-brain barrier permeability to horseradish peroxidase in mice. *Acta Neuropathol.* 86:49–54, 1993.

What is claimed is:

1. A pharmaceutical composition for facilitating passage of compounds through the blood-brain-barrier comprising:

AChE-I4 readthrough spliced variant (SEQ ID No.: 1) or functional analogs comprising at least the 26 C-terminal amino acid residues of the AChE-I4 readthrough splice variant being effective under stress or stress-induced conditions and a pharmaceutically acceptable carrier.

2. A pharmaceutical composition for facilitating the passage of compounds through the blood-brain-barrier comprising:

AChE-14 readthrough splice variant (SEQ ID No.: 1) or functional analogues comprising at least the 26 C-terminal amino acid residues of the AChE-I4 readthrough splice variant being effective in stress or stress-induced conditions in combination with at least one from the group consisting essentially of 14 peptide, adrenaline, atropine, dopamine, or an adrenergic combination and a pharmaceutically acceptable carrier.

3. The pharmaceutical composition as set forth in claim 2 further including a compound to be passaged through the blood-brain barrier.

4. The pharmaceutical composition as set forth in claim 3 wherein said adrenergic combination is an alpha-adrenergic agonist and a β-adrenergic antagonist.

5. The pharmaceutical composition as set forth in claim 4 wherein said alpha-adrenergic agonist is dopamine and said β-adrenergic antagonist is propanolol.

6. A pharmaceutical composition for facilitated administration of a drug through the blood-brain-barrier comprising:

AChE-14 readthrough splice variant (SEQ ID No.: 1) or functional analogues comprising at least the 26 C-terminal amino acid residues of the AChE-I4 readthrough splice variant being effective in stress or stress-induced conditions and a pharmaceutically acceptable carrier.

7. The composition of claim 6 further including at least one stress-inducing agent selected from the group consisting essentially of I4 peptide (SEQ ID No:2), adrenaline, atropine, dopamine, or an adrenergic combination, and a pharmaceutically acceptable carrier.

8. The composition of claim 7 wherein the adrenergic combination is an α adrenergic agonist and a β adrenergic antagonist.

9. The composition of claim 8 wherein the α adrenergic agonist is dopamine and the β adrenergic antagonist is propanolol.

10. The pharmaceutical composition as set forth in claim 7 further including a compound to be passed through the blood-brain-barrier.

* * * * *